United States Patent
Sahasrabudhe et al.

(10) Patent No.: US 12,076,310 B2
(45) Date of Patent: Sep. 3, 2024

(54) COMPOUNDS AND METHODS FOR THE TREATMENT OF ACUTE MYELOGENOUS LEUKEMIA

(71) Applicant: University of Rochester, Rochester, NY (US)

(72) Inventors: Deepak Sahasrabudhe, Rochester, NY (US); Rakesh K. Singh, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 17/835,545

(22) Filed: Jun. 8, 2022

(65) Prior Publication Data
US 2023/0000823 A1 Jan. 5, 2023

Related U.S. Application Data

(60) Provisional application No. 63/208,540, filed on Jun. 9, 2021.

(51) Int. Cl.
*A61K 31/404* (2006.01)
*A61P 35/02* (2006.01)

(52) U.S. Cl.
CPC .......... *A61K 31/404* (2013.01); *A61P 35/02* (2018.01)

(58) Field of Classification Search
CPC .............................. A61K 31/404; A61P 35/00
See application file for complete search history.

(56) References Cited

U.S. PATENT DOCUMENTS 9,290,449 B2 * 3/2016 Toretsky .............. C07D 209/38

FOREIGN PATENT DOCUMENTS

CN 103435606 * 12/2013

OTHER PUBLICATIONS

Ashton, et al., "Gene Sets Identified with Oncogene Cooperativity Analysis Regulate In Vivo Growth and Survival of Leukemia Stem Cells", Cell Stem Cell, vol. 11, No. 3 (2012), pp. 359-372.
Bagger, et al., "BloodSpot: a database of healthy and malignant haematopoiesis updated with purified and single cell mRNA seequencing profiles", Nucleic Acids Research, vol. 47, No. D1 (2019), pp. D881-D885.
Dohner, et al., "Acute Myeloid Leukemia", New England Journal of Medicine, vol. 373, No. 12 (2015), pp. 1136-1152.
Garrido, et al., "Acute myeloid leukemia cells are protected from spontaneous and drug-induced apoptosis by direct contact with a human bone marrow stromal cell line (HS-5)", Experimental Hematology, vol. 29, No. 4 (2001), pp. 448-457.
Gentles, et al., "Association of a Leukemic Stem Cell Gene Expression Signature With Clinical Outcomes in Acute Myeloid Leukemia", Journal of the American Medical Association, vol. 304, No. 24 (2010), pp. 2706-2715.
Jameson, et al., "IQGAP1 scaffold-kinase interaction blockade selectively targets RAS-MAP kinase-driven tumors", Nature Medicine, vol. 19, No. 5 (2013), pp. 626-630.
Johnson, et al., "IQGAP1 regulation and roles in cancer", Cellular Signaling, vol. 21, No. 10 (2009), pp. 1471-1478.
Kurella, et al., "Crystal structure of the GTPase-activating protein-related domain from IQGAP1", Journal of Biological Chemistry, vol. 284, No. 22 (2009), pp. 14857-14865.
Li, et al., "Gastric Hyperplasia in Mice Lacking the Putative Cdc42 Effector IQGAP1", Molecular and Cellular Biiology, vol. 20, No. 2 (2000), pp. 697-701.
Siegel, et al., "Cancer Statistics, 2021", CA: A Cancer Journal for Clinicians, vol. 71, No. 1 (2021), pp. 7-33.
Thein, et al., "Outcome of older patients with acute myeloid leukemia: an analysis of SEER data over 3 decades", Cancer, vol. 119, No. 15 (2013), pp. 2720-2727.
White, et al., "IQGAP1 and Its Binding Proteins Control Diverse Biological Functions", Cellular Signaling, vol. 24, No. 4 (2012), pp. 826-834.

* cited by examiner

*Primary Examiner* — Shobha Kantamneni
(74) *Attorney, Agent, or Firm* — Riverside Law LLP

(57) ABSTRACT

The present disclosure relates to compounds and methods for treating cancer, the methods comprising administering to the subject a compound of formula (1). In some embodiments, the disclosure provides compounds and methods for inhibiting IQGAP1.

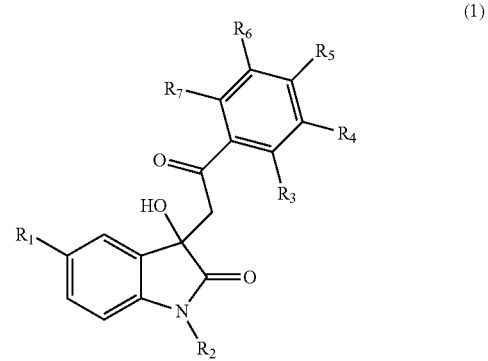

3 Claims, 29 Drawing Sheets
Specification includes a Sequence Listing.

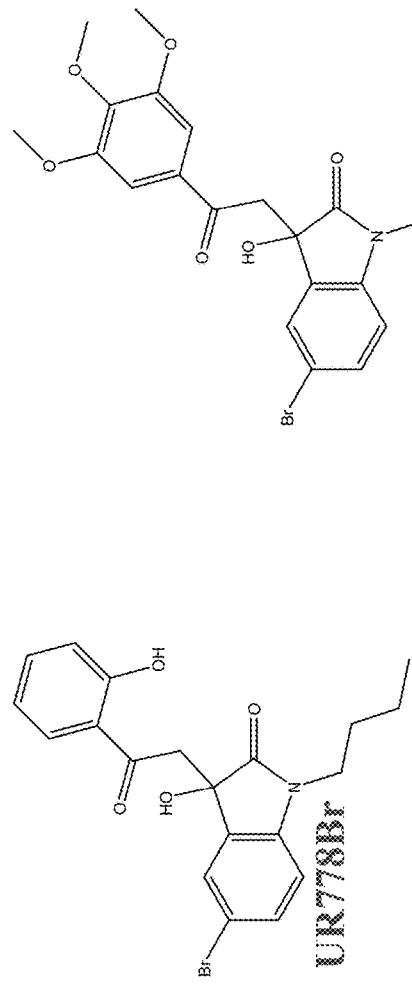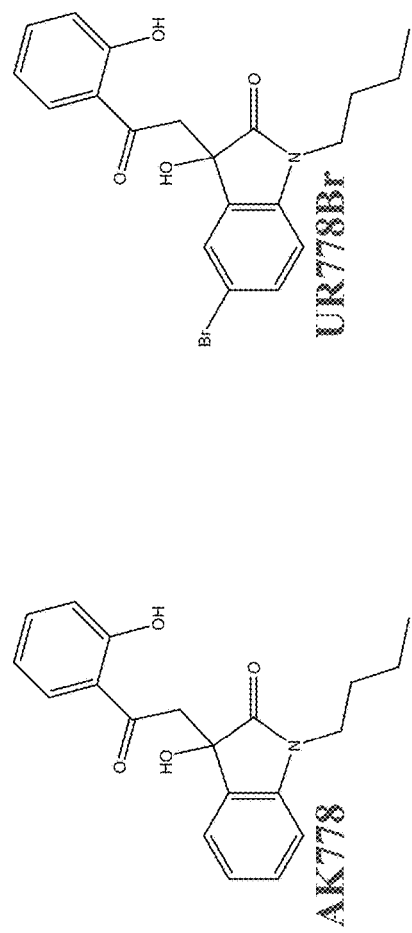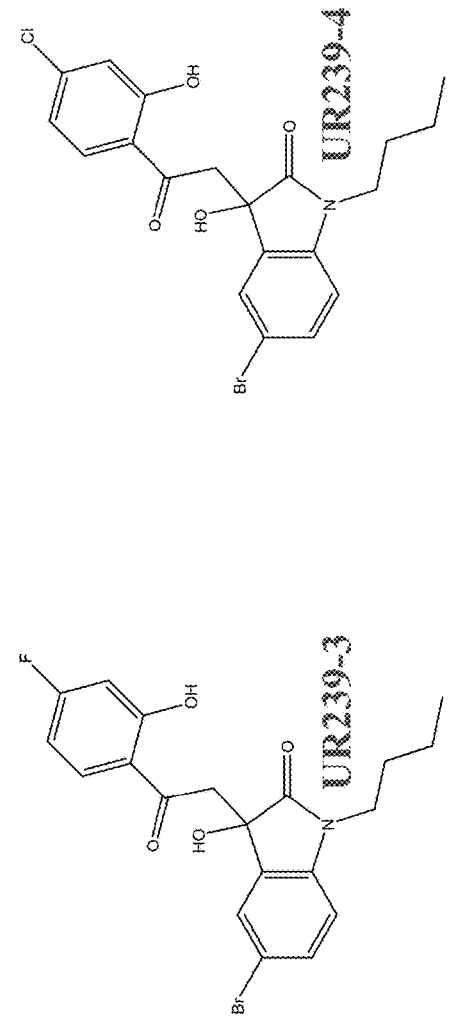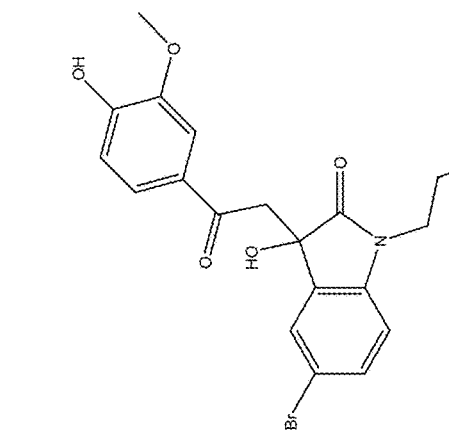
Figure 5

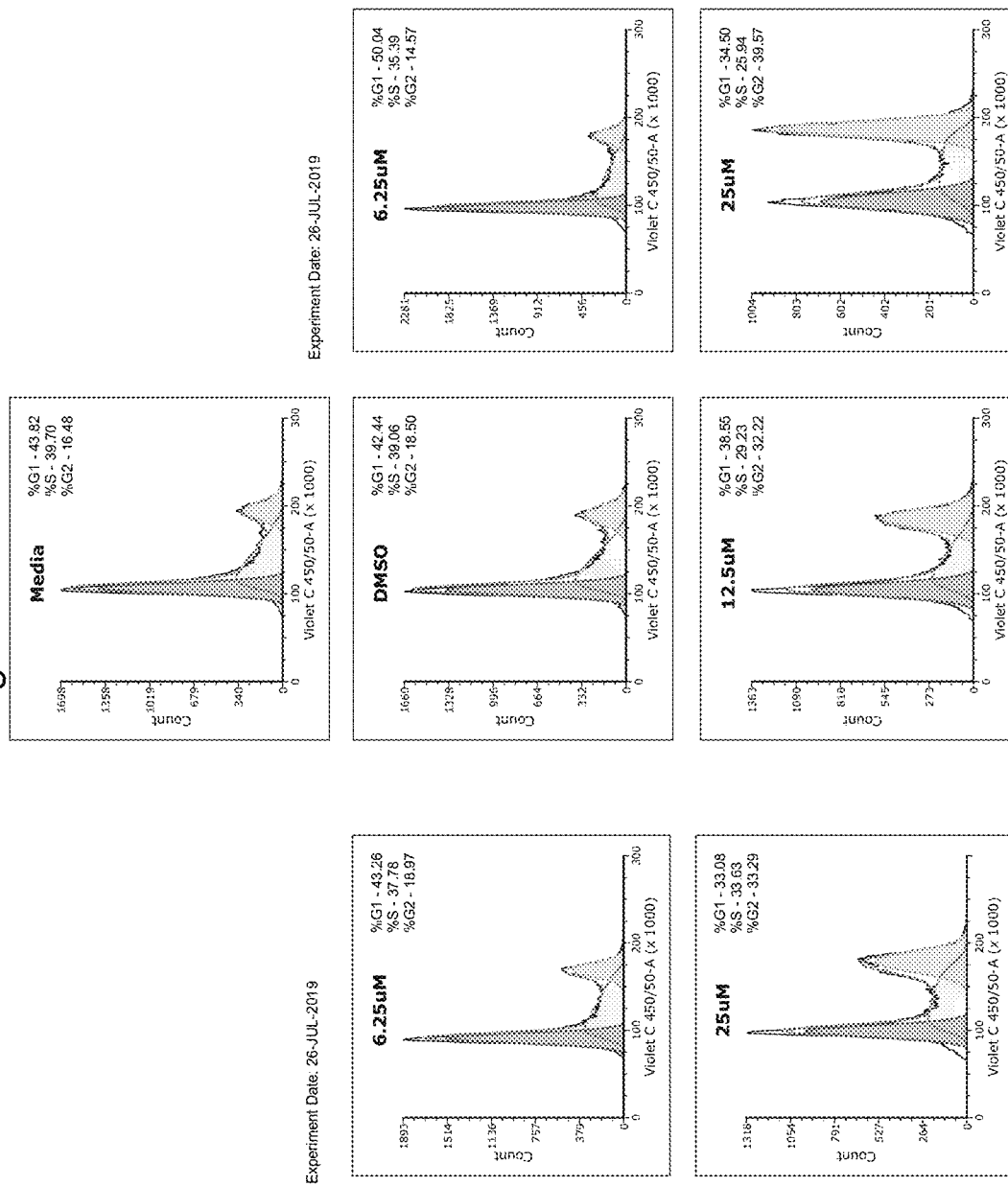

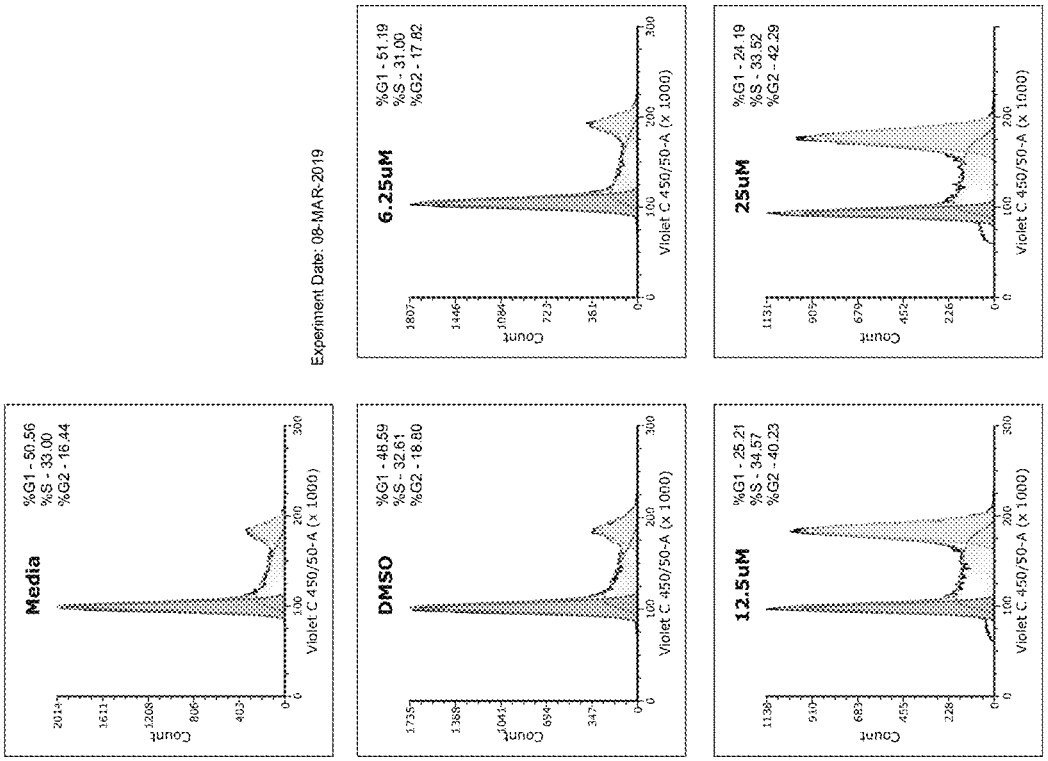
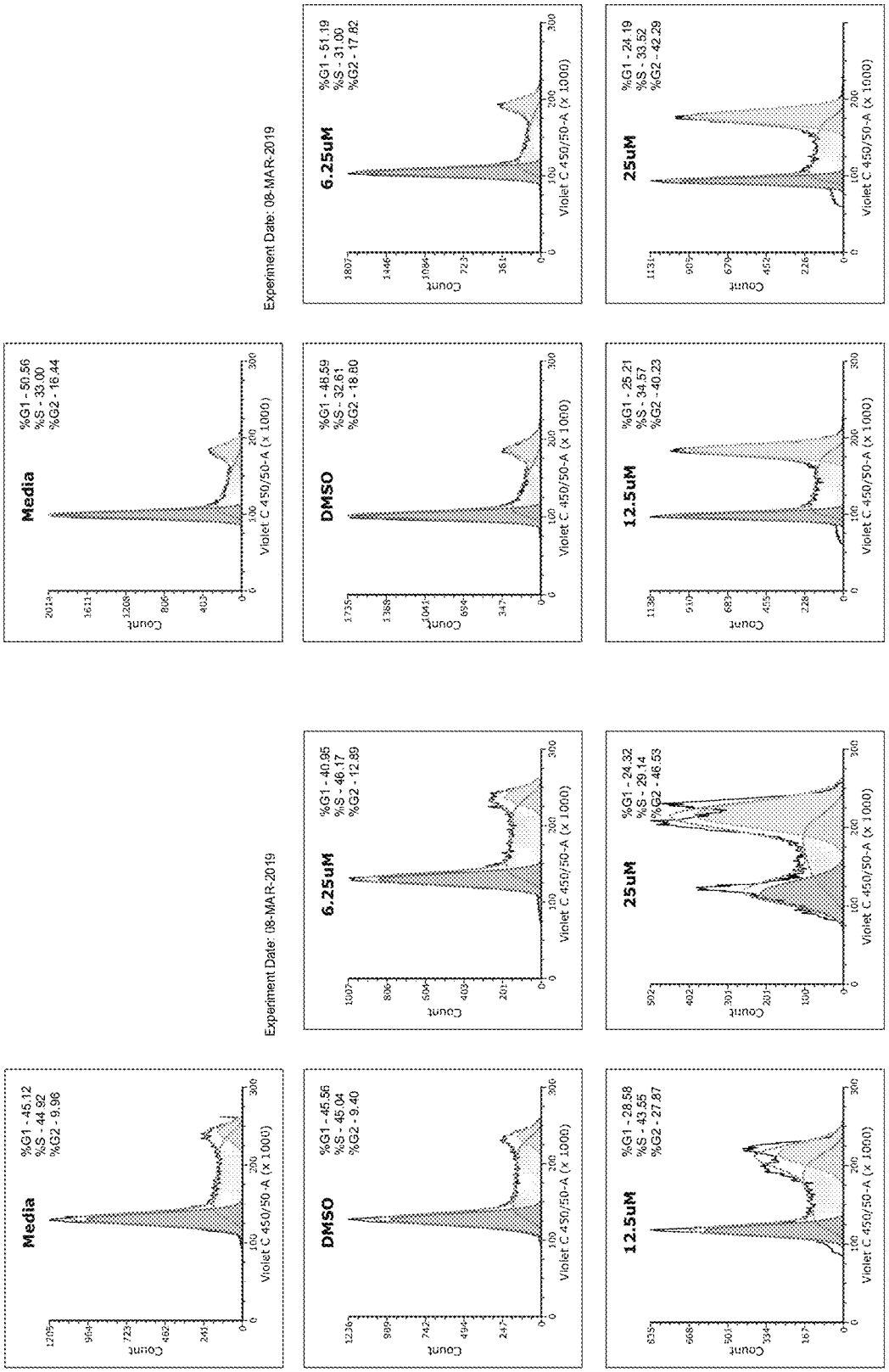

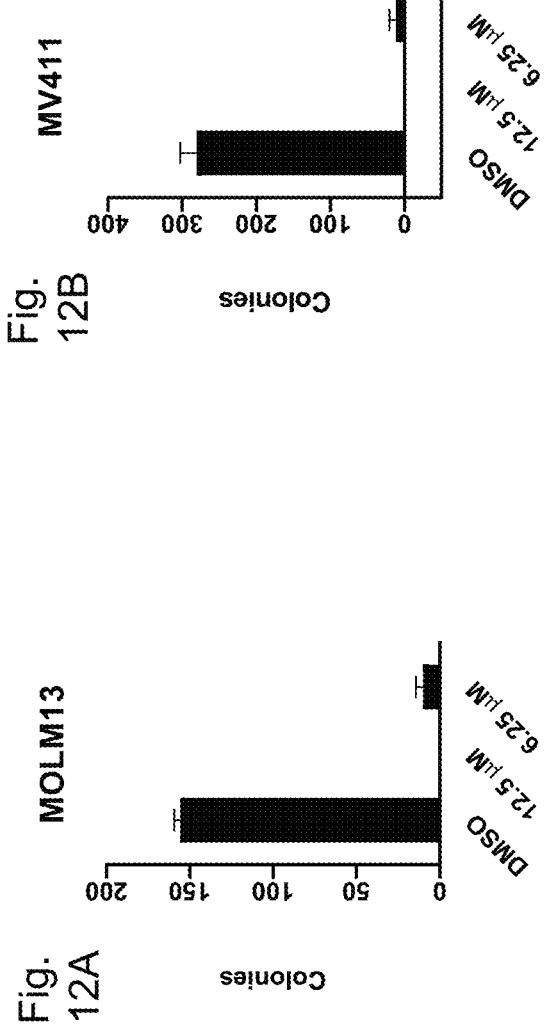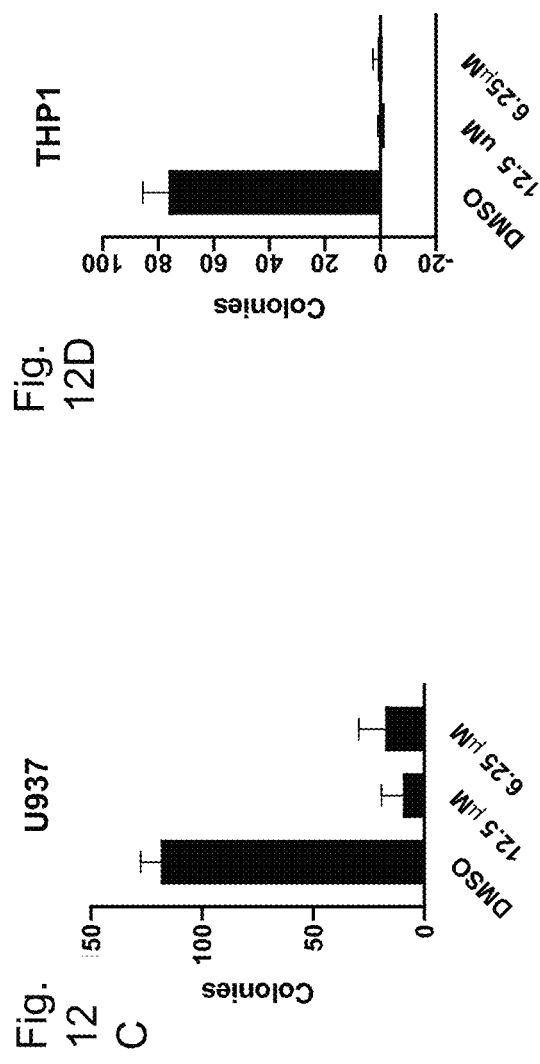

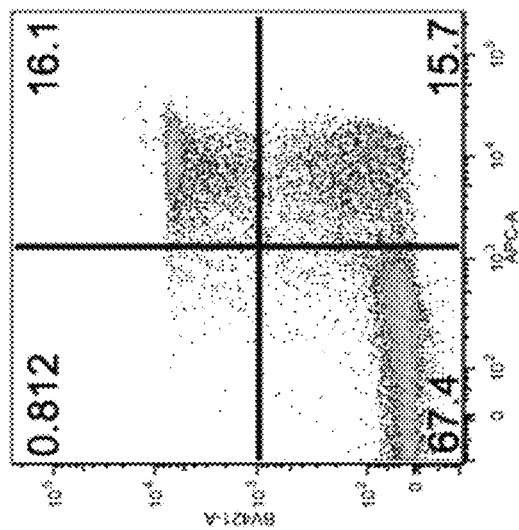
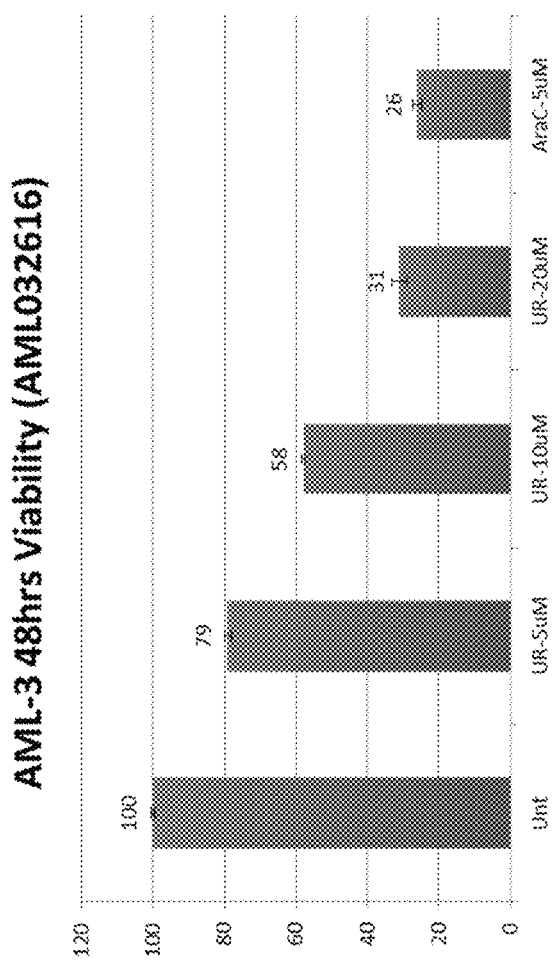
Figure 14

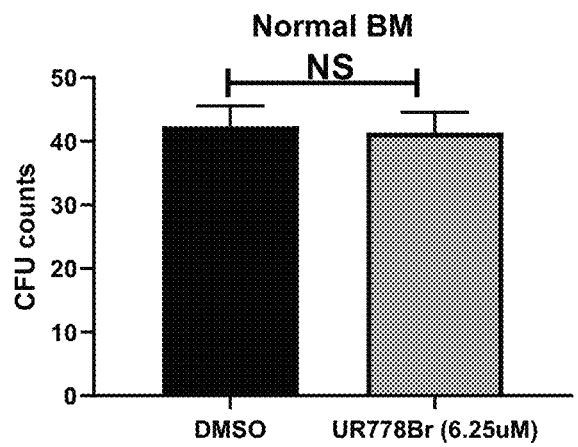
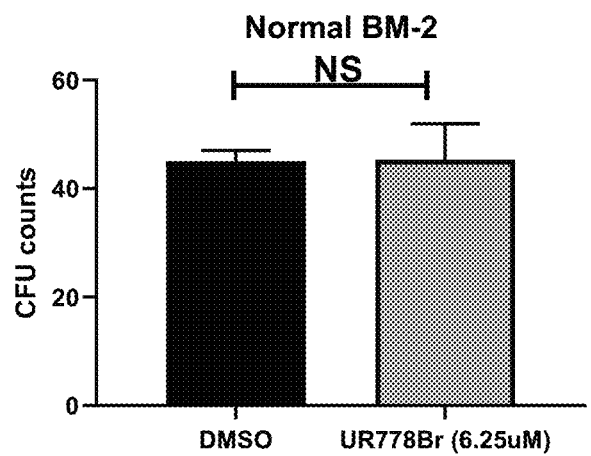
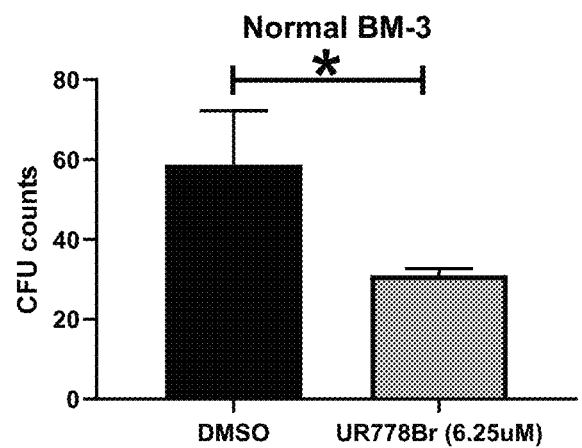
Figure 17

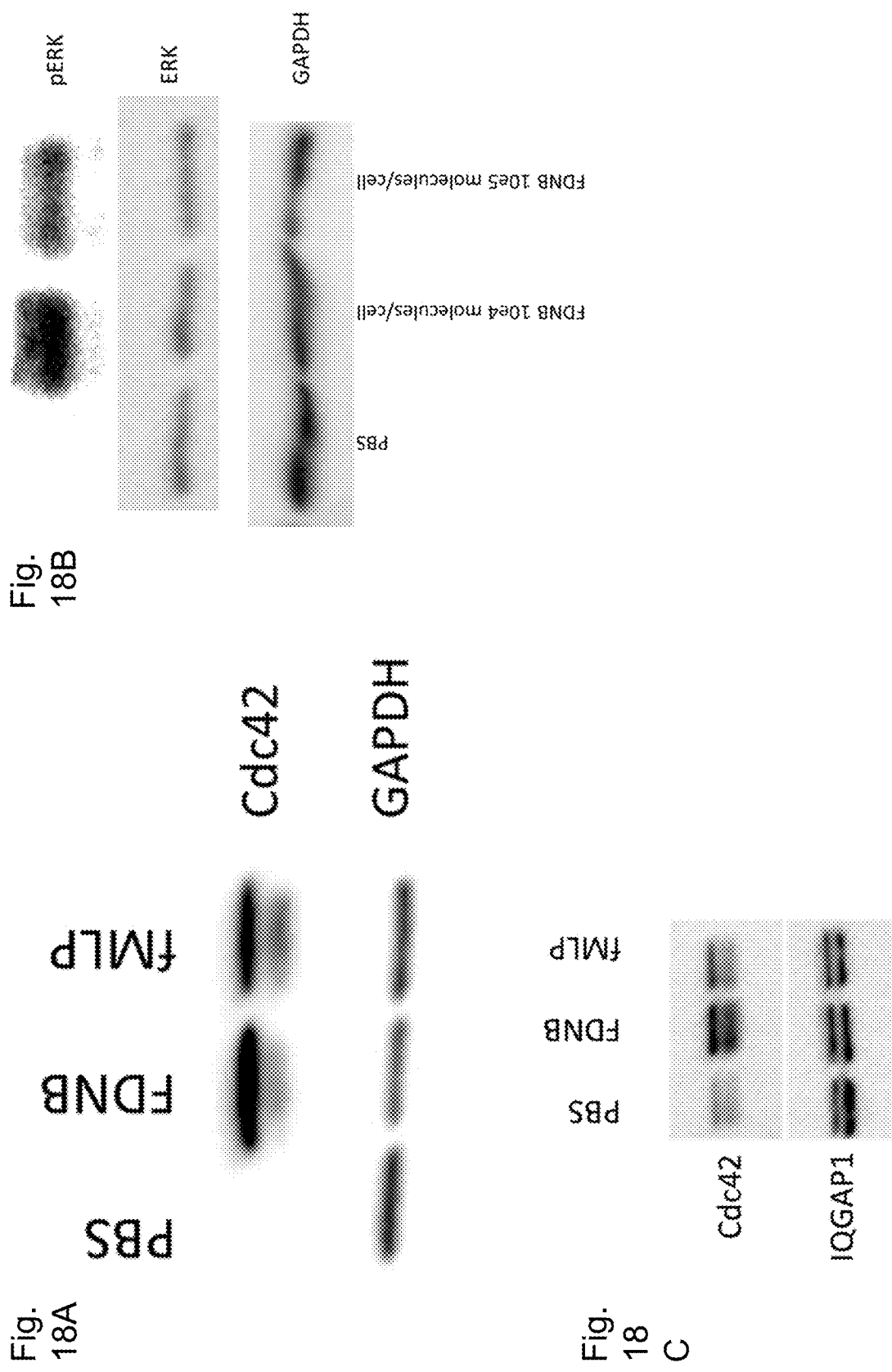

COMPOUNDS AND METHODS FOR THE TREATMENT OF ACUTE MYELOGENOUS LEUKEMIA

CROSS-REFERENCE TO RELATED APPLICATIONS

The present application claims priority to U.S. Provisional Application No. 63/208,540, filed Jun. 9, 2021, which is incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "204606-0137-00US_SequenceListing" having a creation date of Jun. 8, 2022, and having a size of 918 bytes. The sequence listing submitted via EFS-Web is part of the specification and is herein incorporated by reference in its entirety.

BACKGROUND OF THE INVENTION

Acute myeloid leukemia (AML) is a malignancy which arises in a primitive hematopoietic stem cell and has very poor prognosis (Hartmut et al., NEJM, 2015, 373(12):1136-1152). Two-thirds of young adults and 90% of patients over 60 die of their disease. There are about 30,000 new cases of AML diagnosed per year in the USA, and the incidence is rising given the aging of the population. Further, AML is emerging as the leading cause of leukemia-related deaths in the US (Siegel et al., Cancer Statistics, 2021. CA: a Cancer Journal for Clinicians. 2021, 71(1):7-33)

AML is a heterogeneous disease characterized by cytogenetic and molecular markers, many of which cannot be specifically targeted to date. Current therapies have plateaued in their responses and new therapies with newer mode(s) of action are urgently needed, particularly among older patients since the median age at onset is 70 years (Thein et al., Cancer, 2013, 119(15): 2720-2727). The current standard-of-care repertoire of therapies is often able to achieve remission or partial remission, but disease relapse and progression occur in the majority of cases. Most newly developed targeted therapies such as bcl-2 or IDH1/2 inhibitors do not induce durable remissions when used in isolation or combination, and many older patients are not able to undergo intensive chemotherapy or stem cell transplantation due to higher morbidity and mortality in older individuals.

IQGAP1 is a 190 kDa scaffolding protein. It regulates multiple cellular activities such as cytoskeletal organization, cell-cell adhesion, migration, transcription, and signal transduction (White et al., Cellular Signaling, 2012, 24(4): 826-834). It is over expressed in primary human AML across cytogenetic subtypes compared to normal hematopoietic stem cell controls (BloodSpot, http://servers.binf.ku.bloodspot). It is also over expressed in solid tumors such as glioma, colon-, gastric- lung-, ovarian-, and head and neck cancer (Johnson et al., Cellular Signaling, 2009, 21(10): 1471-78). Over expression is associated with an aggressive clinical course in glioma, gastric- and ovarian cancer. However, IQGAP1 null mutant mice are born at normal frequency and show no obvious defects during development or for most of their adult life8 except late-onset gastric hyperplasia suggesting that inhibition of IQGAP1 by pharmacologic means may not be very toxic.

Thus, there is a need in the art for improved compositions and methods for the treatment and prevention of acute myeloid leukemia. This invention satisfies this unmet need.

SUMMARY OF THE INVENTION

In one aspect, the disclosure provides methods of treating cancer in a subject. In one embodiment, the method comprises administering to a subject a compound of formula (1):

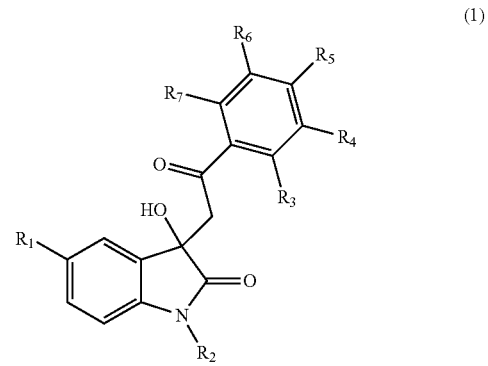

(1)

wherein $R_1$ is selected from the group consisting of hydrogen and a halogen; $R_2$ is an $C_1$-$C_4$ alkyl group; $R_3$-$R_7$ are each independently selected from the group consisting of a hydrogen, hydroxyl, a halogen, and an alkoxy group.

In one embodiment, $R_1$ is selected from the group consisting of hydrogen and bromine. In one embodiment, $R_2$ is a butyl group. In one embodiment, $R_3$-$R_7$ are each independently selected from the group consisting of hydrogen, methoxy, hydroxyl, fluorine and chlorine. In one embodiment, $R_7$ is hydrogen. In one embodiment, $R_3$ is hydroxyl.

In one embodiment, the compound of formula (1) is:

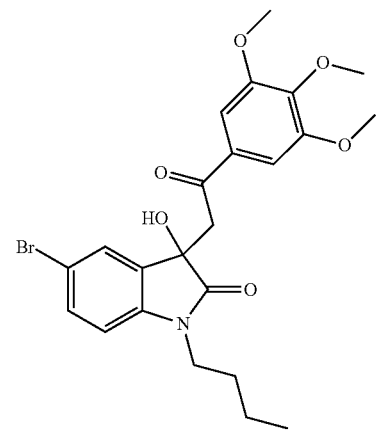

3
-continued

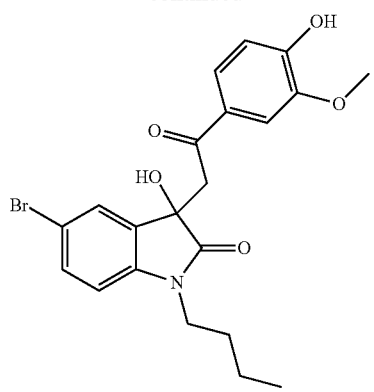

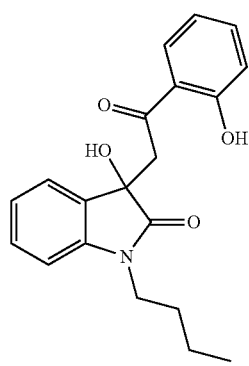

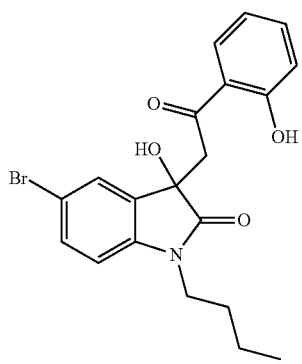

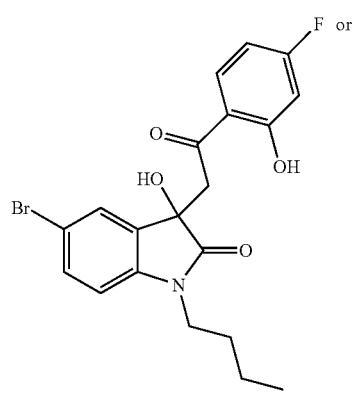

4
-continued

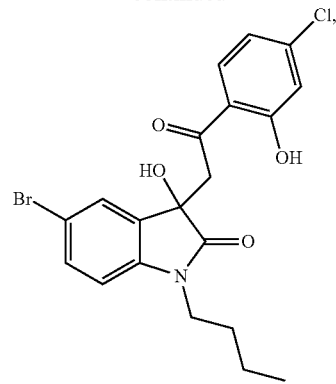

or a salt thereof.

In one embodiment, the compound of formula (1) is

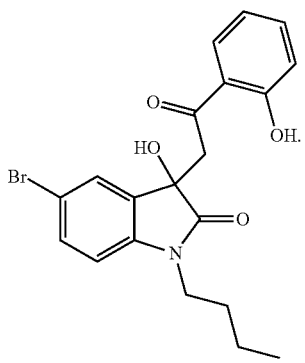 [SMILES: CCCCN1C(=O)C(O)(CC(=O)c2ccccc2O)c2cc(Br)ccc21]

In one embodiment, the cancer is selected from the group consisting of acute myeloid leukemia (AML), colon cancer, glioma, non-small cell lung cancer, and gastric cancer. In one embodiment, the cancer is AML.

In one aspect, the disclosure provides methods of inhibiting IQGAP1 activity in a subject. In one embodiment, the method comprises administering to a subject a compound of formula (1):

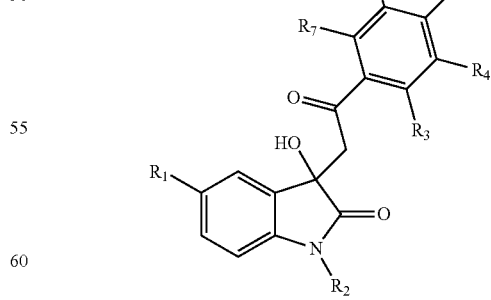

(1)

wherein $R_1$ is selected from the group consisting of hydrogen and a halogen; $R_2$ is an $C_1$-$C_4$ alkyl group; $R_3$-$R_7$ are each independently selected from the group consisting of a hydrogen, hydroxyl, a halogen, and an alkoxy group.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 5 depicts the structure of AK778, its structural analog UR778Br, and additional in-house generated analogs of UR778Br with chemical modifications.

FIG. 6A depicts a schematic outline of rabbit immunization experiments with untreated or FDNB-treated white blood cells (WBC). FIG. 6B depicts exemplary immunoblotting results demonstrating that serum from rabbits immunized with FDNB modified WBCs recognized a different set of antigens than the ones by serum from rabbit immunized with unmodified WBCs. FIG. 6C depicts a schematic of the strategy of depletion followed by enrichment prior to proteomic analysis of the affinity purified lysates of primary AML samples. FIG. 6D depicts exemplary immunoblotting results demonstrating expression of IQGAP1 in primary AML samples. FIG. 6E depicts exemplary immunoblotting results demonstrating expression of IQGAP1 in primary AML samples as compared to normal bone marrow.

FIG. 7D depicts exemplary results demonstrating overexpression of IQGAP1 in AML from the curated, publicly available BloodSpot data set.

FIG. 11A through 11E depict exemplary flow cytometry results demonstrating cell cycle arrest. FIGS. 11A through 11D show that exposure of MOLM13 (FIG. 11A), MV411 (FIG. 11B), U937 (FIG. 11C) and THP1 (FIG. 11D) leukemia cell lines to increasing concentrations of UR778Br for 24 hours results in dose-dependent arrest in G2/M phase of the cell cycle. FIG. 11E demonstrates that exposure of each of the four cell lines to 25 µM UR778B2 for 24 hours results in expression of cleaved PARP, a marker of apoptosis.

FIGS. 12A through 12D depict exemplary results demonstrating the UR778Br resulted in inhibition of the colony formation units of MOLM13 (FIG. 12A), MV411 (FIG. 12B), U937 (FIG. 12C) and THP1 (FIG. 12D) leukemia cell lines at concentration of 6.25p M.

FIG. 17 depicts exemplary results demonstrating that the majority of normal bone marrow samples do not exhibit reduced colony formation in response to 6.25 µM UR778Br.

FIG. 18A through FIG. 18C depict the effect of fluorodinitrobenzene (FDNB). FIG. 18A depicts the effect of FDNB on phosphorylation of Cdc42 in white blood cells (WBCs). FIG. 18B depicts the effect of FDNB on WBCs. FIG. 18C depicts the effect of exposure to FDNB on activation of Cdc42 in WBCs.

DETAILED DESCRIPTION

Figure 1:
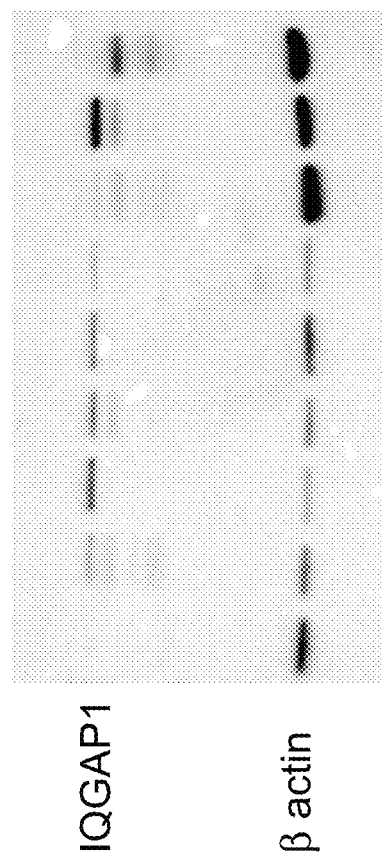
FIG. 1 depicts exemplary immunoblotting results demonstrating IQGAP1 and GAPDH expression in clinical AML samples.

In one aspect, the disclosure is based in part on the unexpected finding of novel compounds which inhibit IQGAP1. In one embodiment, these compounds are useful for treating diseases and/or disorders associated with IQGAP1 overexpression. For example, in one embodiment, the compounds of the disclosure may treat cancer. In some embodiments, the compounds may treat acute myeloid leukemia (AML), colon cancer, glioma, non-small cell lung cancer, and/or gastric cancer.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20%, ±10%, +5%, +1%, or ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

A "therapeutic" treatment is a treatment administered to a subject who exhibits signs or symptoms of pathology disease or disorder, for the purpose of diminishing or eliminating those signs or symptoms.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell from a patient (e.g., for diagnosis or ex vivo applications), who has a disease or disorder contemplated herein, a sign or symptom of a disease or disorder contemplated herein or the potential to develop a disease or disorder contemplated herein, with the purpose to cure, heal, alleviate, relieve, alter, remedy, ameliorate, improve or affect a disease or disorder contemplated herein, the signs or symptoms of a disease or disorder contemplated herein or the potential to develop a disease or disorder contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a sufficient amount of an agent to provide the desired biological or physiologic result. That result may be reduction and/or alleviation of a sign, a symptom, or a cause of a disease or disorder, or any other desired alteration of a biological system. An appropriate effective amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition, or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "potency" refers to the dose needed to produce half the maximal response ($ED_{50}$).

As used herein, the term "efficacy" refers to the maximal effect ($E_{max}$) achieved within an assay.

As used herein, "activity" includes physiological activity, binding affinity, and/or the enzymatic activity of a molecule.

As used herein, "IQGAP1" refers to IQ Motif Containing GTPase Activating Protein 1.

As used herein, "associated" refers to coincidence with the development or manifestation of a disease, condition, or phenotype. Association may be due to, but is not limited to, genes responsible for housekeeping functions, those that are part of a pathway that is involved in a specific disease, condition, or phenotype and those that indirectly contribute to the manifestation of a disease, condition or phenotype.

As used herein, the term "cancer" refers to any of various types of malignant neoplasms, most of which invade surrounding tissues, may metastasize to several sites and are likely to recur after attempted removal and to cause death of the patient unless adequately treated. As used herein, neoplasia comprises cancer. Representative cancers include, for example, squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias, including non-acute and acute leukemias, such as acute myelogenous leukemia, acute lymphocytic leukemia, acute promyelocytic leukemia (APL), acute T-cell lymphoblastic leukemia, T-lineage acute lymphoblastic leukemia (T-ALL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas, among others, which may be treated by one or more compounds of the present invention.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized, and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties.

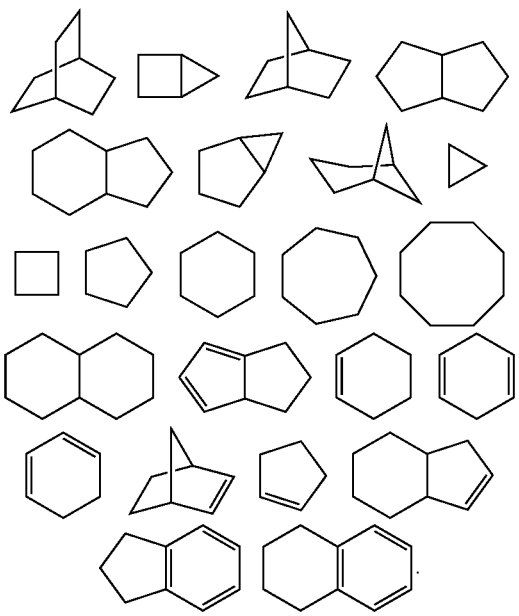

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

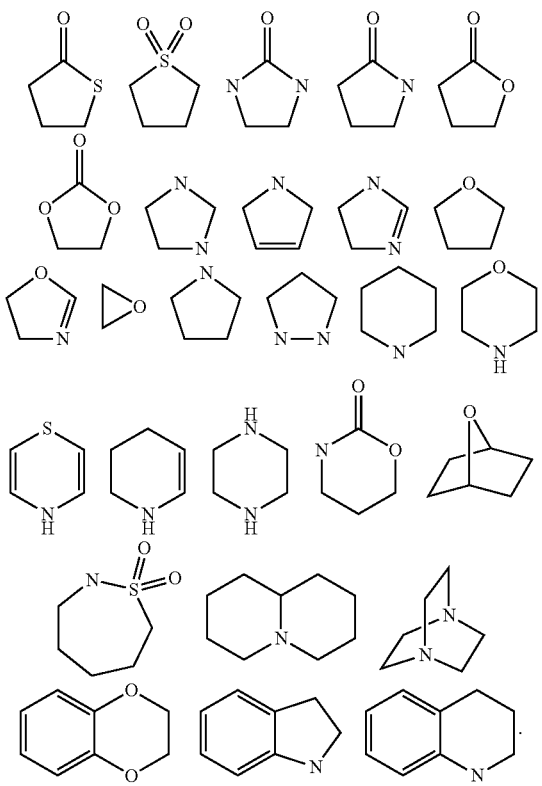

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. In one embodiment, aryl-($C_1$-$C_3$)alkyl is aryl-$CH_2$— or aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

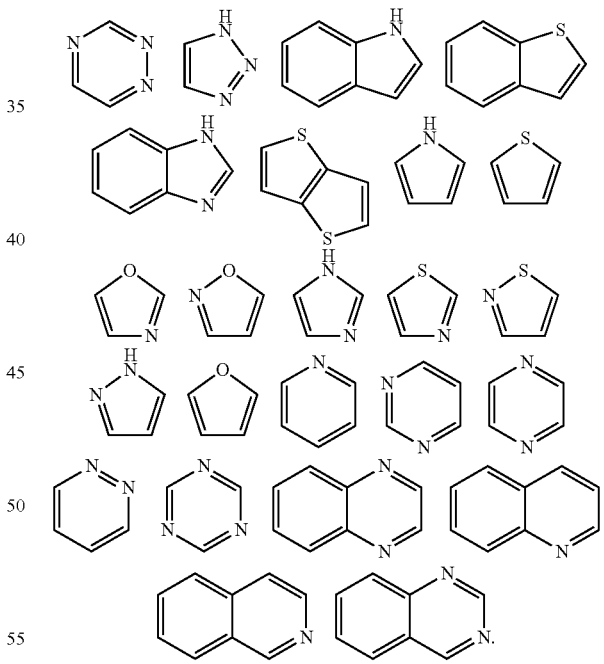

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]2. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds of the present disclosure may be synthesized using techniques well-known in the art of organic synthesis. The starting materials and intermediates required for the synthesis may be obtained from commercial sources or synthesized according to methods known to those skilled in the art.

In one aspect, the disclosure provides compounds of formula (1) or a pharmaceutically acceptable salt, solvate, hydrate or stereoisomer thereof:

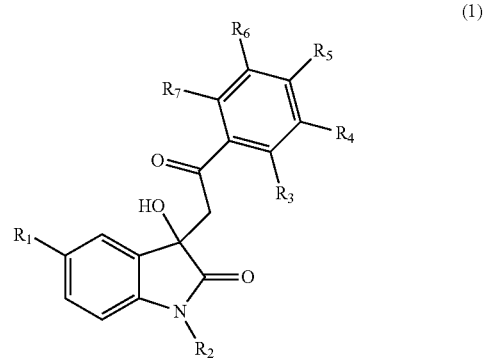

(1)

wherein R$_1$ is selected from the group consisting of hydrogen and a halogen; R$_2$ is an C$_1$-C$_4$ alkyl group; and R$_3$-R$_7$ are each independently selected from the group consisting of a hydrogen, hydroxyl, a halogen, and an alkoxy group.

In one embodiment, R$_1$ is selected from the group consisting of hydrogen and bromine. In one embodiment, R$_1$ is hydrogen. In one embodiment, R$_1$ is bromine.

In one embodiment, R$_2$ is a C$_1$-C$_5$ alkyl group. In one embodiment, R$_2$ is a butyl group. In one embodiment, R$_2$ is a straight chain butyl group.

In one embodiment, R$_3$-R$_7$ are each independently selected from the group consisting of hydrogen, methoxy, hydroxyl, fluorine and chlorine. In one embodiment, R$_3$ is hydroxyl. In one embodiment, R$_7$ is hydrogen.

In one embodiment, the compound of formula (1) is selected from the group consisting of:

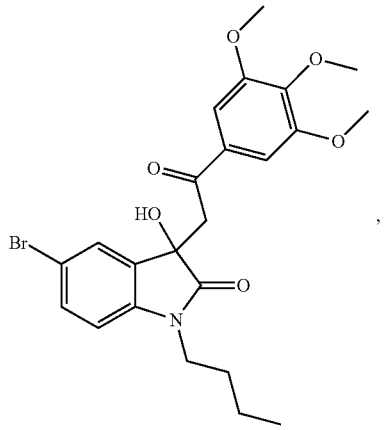

,

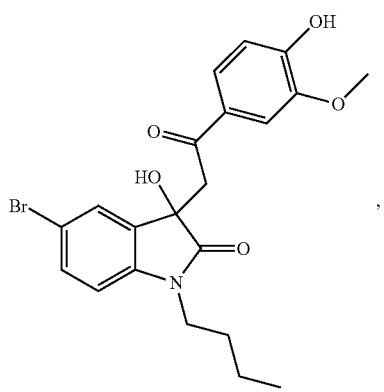

,

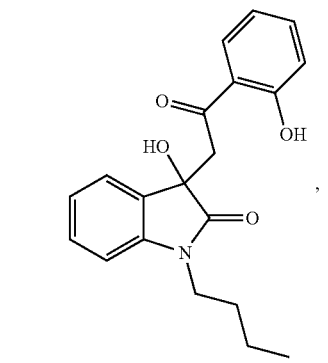

,

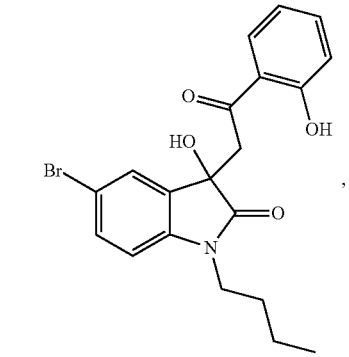

,

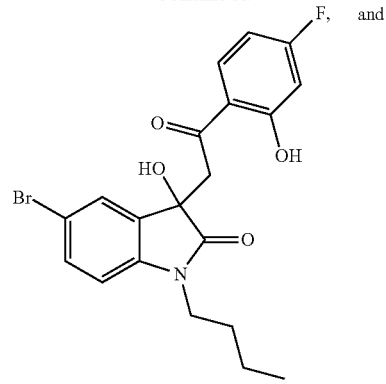

,

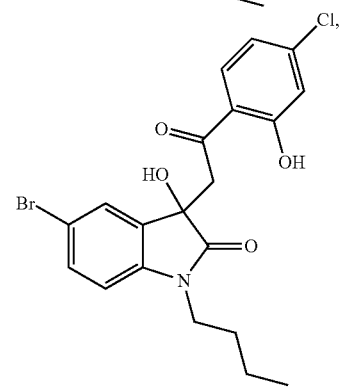

or a salt thereof.

In one embodiment, the compound of formula (1) is

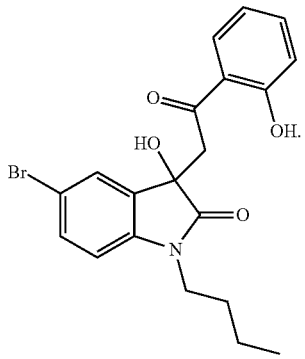 [SMILES: CCCCN1C(=O)C(O)(CC(=O)c2ccccc2O)c2cc(Br)ccc21]

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference in their entirety). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

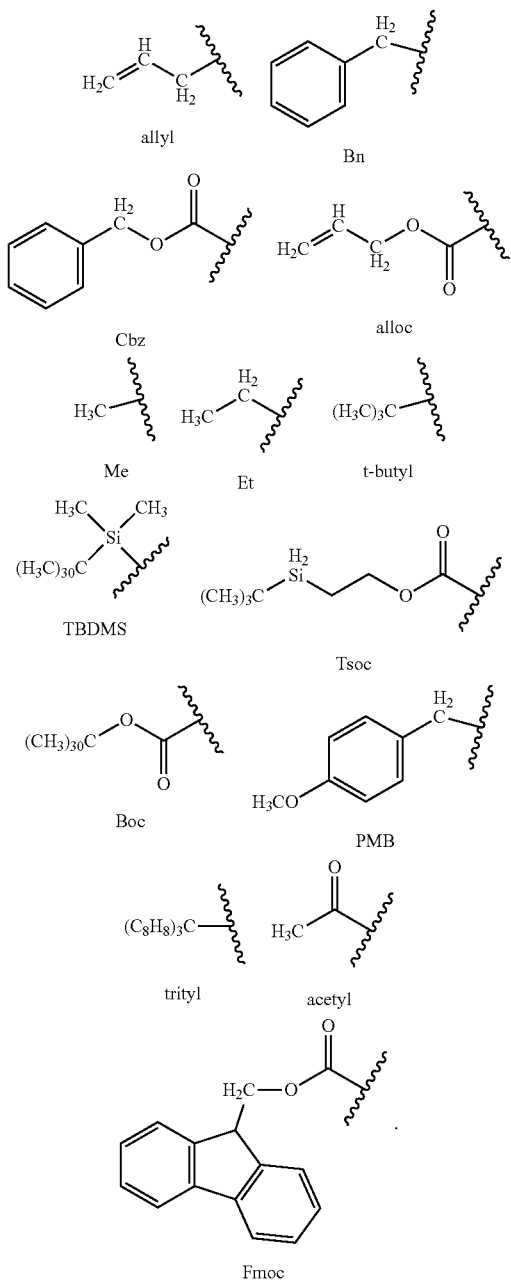

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Methods

In some embodiments, the disclosure provides methods of inhibiting IQGAP1 activity in a subject in need thereof. In one embodiment, the method comprises administering to the subject an effective amount of a composition comprising a compound of the disclosure. In one embodiment, the compound of the disclosure binds to IQGAP1 thereby inhibiting its activity.

In one embodiment, the disclosure provides method of treating or preventing a disease or disorder associated with IQGAP1 activity. As used herein, the term "disease or disorder associated with IQGAP1 activity" refers to any disease, disorder, or condition which is caused or characterized by abnormal IQGAP1 enzymatic activity or IQGAP1 overexpression. Exemplary diseases or disorders associated with IQGAP1 activity include, but are not limited to cancer.

In one embodiment, the disclosure provides methods comprising administering to a subject a compound of the disclosure. In one embodiment, the subject has a disease or disorder associated with IQGAP1 activity. In one embodiment, the subject has cancer.

In one embodiment, the disclosure provides methods of treating cancer in a subject in need thereof. In one embodiment, the method comprises administering to the subject an effective amount of a compound of the disclosure.

In one embodiment, the method further comprises administering to the subject at least one additional therapeutic agent. In one embodiment, the therapeutic agent is selected from the group consisting of a chemotherapy, chemotherapeutic agent, radiation therapy, hormonal therapy, and any combination thereof.

The disclosed compounds can be used to slow the rate of primary tumor growth. The disclosed compounds can also be used to prevent, abate, minimize, control, and/or lessen tumor metastasis. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

In one embodiment, the cancer is associated with or caused by overexpression of IQGAP1. The following are non-limiting examples of cancers that can be treated by the disclosed methods and compositions: Acute Lymphoblastic; Acute Myeloid Leukemia; Adrenocortical Carcinoma; Adrenocortical Carcinoma; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma; Brain Tumor, Adult; Brain Tumor, Brain Stem Glioma; Brain Tumor, Central Nervous System Atypical Teratoid/Rhabdoid Tumor; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma; Cervical Cancer; Chordoma;

Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Brain Stem; Glioma, Cerebral Astrocytoma; Glioma, Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macrobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Adult Acute Myeloid Leukemia; Childhood Acute Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the cancer is acute myeloid leukemia (AML), colon cancer, glioma, non-small cell lung cancer, and gastric cancer. In one embodiment, the cancer is AML.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation, or catheterization. Any administration may be a single application of a composition of invention or multiple applications. Administrations may be to single site or to more than one site in the individual to be treated. Multiple administrations may occur essentially at the same time or separated in time.

In one embodiment, the invention includes a method comprising administering a combination of inhibitor compounds described herein. In certain embodiments, the method has an additive effect, wherein the overall effect of administering the combination of inhibitor compounds is approximately equal to the sum of the effects of administering each individual inhibitor compound. In other embodiments, the method has a synergistic effect, wherein the overall effect of administering a combination of inhibitor compounds is greater than the sum of the effects of administering each individual inhibitor compound. A synergistic effect may be calculated, for example, using suitable methods such as, for example, the Sigmoid-Emax equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The method comprises administering a combination of inhibitors in any suitable ratio. For example, in one embodiment, the method comprises administering three individual inhibitors at a 1:1:1 ratio. In one embodiment, the method comprises administering two individual inhibitors at a 1:1 ratio. However, the method is not limited to any particular ratio. Rather any ratio that is shown to be effective is encompassed.

Combination Therapy

The compounds of the present invention may be useful in combination with one or more additional compounds. In certain embodiments, these additional compounds may comprise compounds of the present invention or therapeutic agents which are known anti-diabetic agents. In certain embodiments, the anti-diabetes agent may comprise compounds useful for treating diabetes. Such compounds include, but are not limited to, compounds which are known to treat, prevent, or reduce the symptoms of cancer.

In some embodiments of the method for treating cancer in an subject in need thereof, comprises administering an effective amount of a compound of the invention to the subject prior to, concurrently with, or subsequently to the treatment with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The inhibitors of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine, and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine;

spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine;

triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Administration/Dosage/Formulations

The regimen of administration may affect what constitutes an effective amount. The therapeutic formulations may be administered to the subject either before or after the onset of a disease or infection. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient or subject, such as a mammal, (e.g., human), may be carried out using known procedures, at dosages and for periods of time effective to treat the disease or infection in the patient. An effective amount of the therapeutic compound necessary to achieve a therapeutic effect may vary according to factors such as the state of the disease or disorder in the subject; the age, sex, and weight of the subject; and the ability of the therapeutic compound to treat a disease in the subject. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular subject, composition, and mode of administration, without generating excessive side effects in the subject.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of a disease or infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the subject, the current medical condition of the subject and the severity of the disease in the subject being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the subject from about one to about five times per day or more. In various embodiments, the compositions of the invention are administered to the subject, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any subject is determined by the medical professional taking all other factors about the subject into account.

In the case wherein the subject's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the subject's condition has occurred, a maintenance dose is administered if necessary. Subsequently, the dosage or the frequency of administration, or both, may be reduced to a level at which the improved disease is retained. In some embodiments, a subject may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent a disease or infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intratumoral, intrapulmonary, intraduodenal, intragastrical, intrathecal, subcutaneous, intramuscular, intradermal, intraarterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for parenteral administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets, and gel caps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters, or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions, or emulsions in an oily or aqueous vehicle, optionally containing other formulatory agents such as suspending, stabilizing and/or dispersing agents may be used.

Controlled Release Formulations

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples, therefore, specifically point out certain embodiments of the present invention, and are not to be construed as limiting in any way the remainder of the disclosure.

Example 1: A Novel Small Molecule Inhibitor of Signaling Pathways in AML

In the present Example an approach is outlined for the development of UR778Br, a small molecule inhibitor of IQGAP1, a scaffolding protein, for treatment of AML. shRNA knockdown of IQGAP1 blocked proliferation and colony formation potential of K562, MV411, and THP1 leukemia cell lines providing critical proof-of-concept that IQGAP1 can be targeted to control AML progression. However, small molecule inhibitors of IQGAP1 have yet to be developed.

To target IQGAP1, a virtual screening was conducted of 212,966 small molecules with drug-like characteristics (MW between 100-800 g/mol) and four potential 'hits' were selected. A focused library of close structural derivatives of the best hit was screened to select UR778Br (MW 418.29 g/mol), a potent small molecule inhibitor of IQGAP1. In this Example, proof-of-concept data is provided showing that UR778Br inhibits the proliferation and colony formation potential of leukemia cells. At similar concentrations it had limited effect of colony formation by normal bone marrow cells. Therefore, it can be considered as the lead compound of a potential new class of drugs for the treatment of AML. Studies to validate the efficacy of UR778Br in standard in-vivo models are proposed.

This is the first systematic effort in the disclosed literature to develop a small molecule inhibitor against IQGAP1. The data presented show that it was essential for the survival and proliferation of AML. Thus, it is demonstrated that IQGAP1 is targetable and that small molecule inhibitors can be developed against it to yield a new therapeutic class of drugs in AML as well as solid tumors.

Results

IQGAP1: A therapeutic target in AML: Scaffolding protein IQGAP1 is involved in many signaling pathways. It is expressed in clinical AML samples (FIG. 1).

Figure 7A:
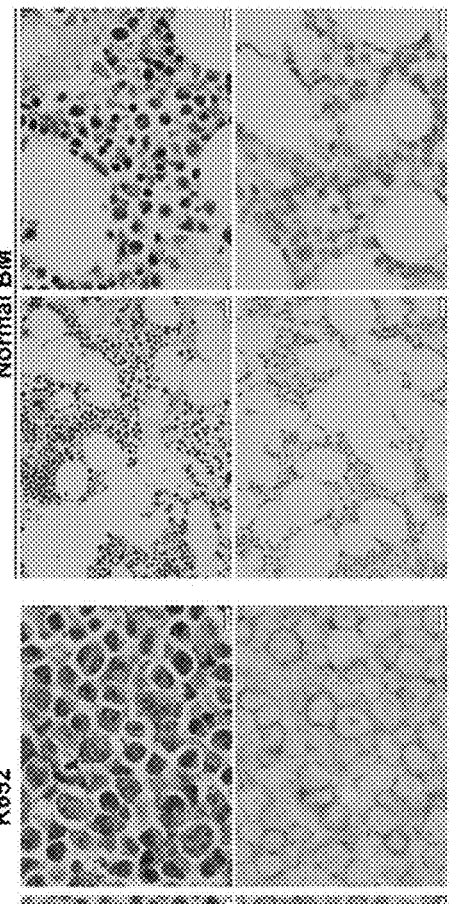
FIGS. 7A through 7D depict exemplary results demonstrating overexpression of IQGAP1 in AML. H&E staining and immunohistochemical staining for IQGAP1 was performed on three leukemia cell-lines, MV411, THP1 and K562 (FIG. 7A), two normal subjects (FIG. 7B) and bone marrow from two AML patients, AML #1 and AML #2 (FIG. 7C).
Figure 7B:
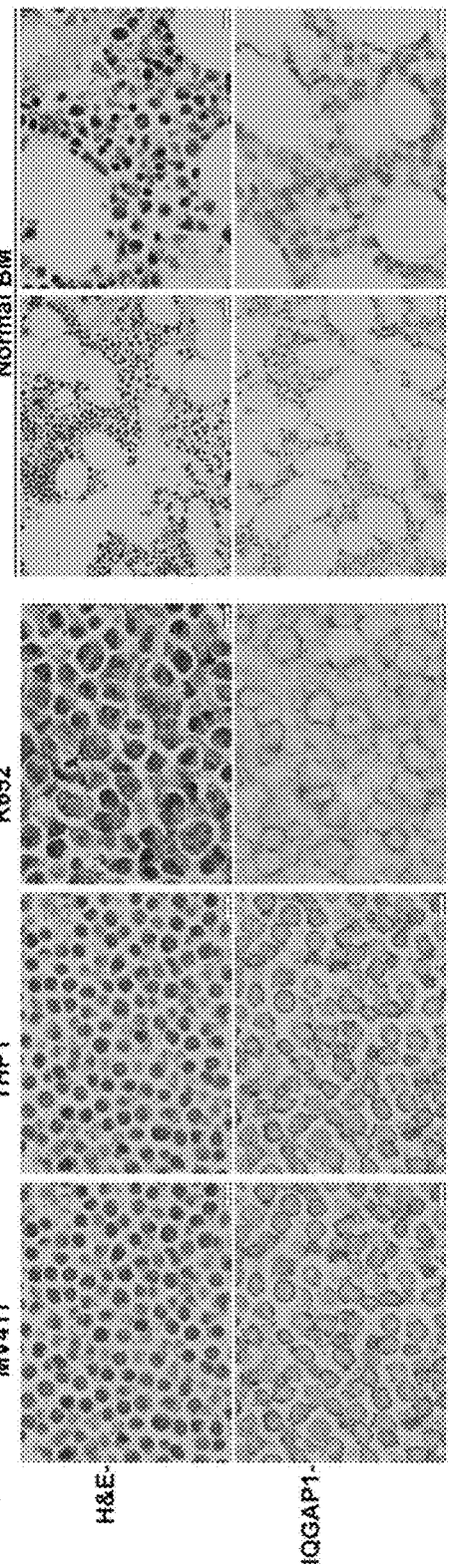
Figure 7C:
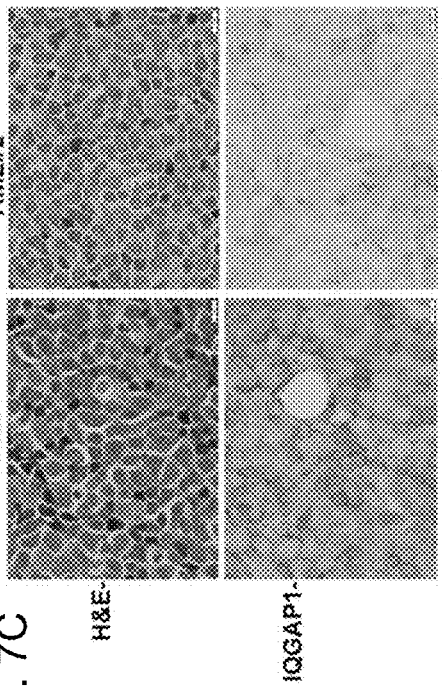
Figure 7D:
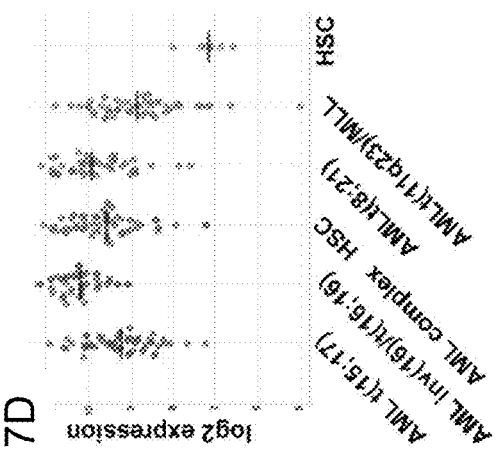

Immunohistochemical analysis showed overexpression in AML compared to normal bone marrow (FIG. 7B and FIG. 7C). BloodSpot analysis showed increased IQGAP1 mRNA expression in primary human AML across cytogenetic subtypes in comparison with normal HSC controls (FIG. 7D).

Figure 2:
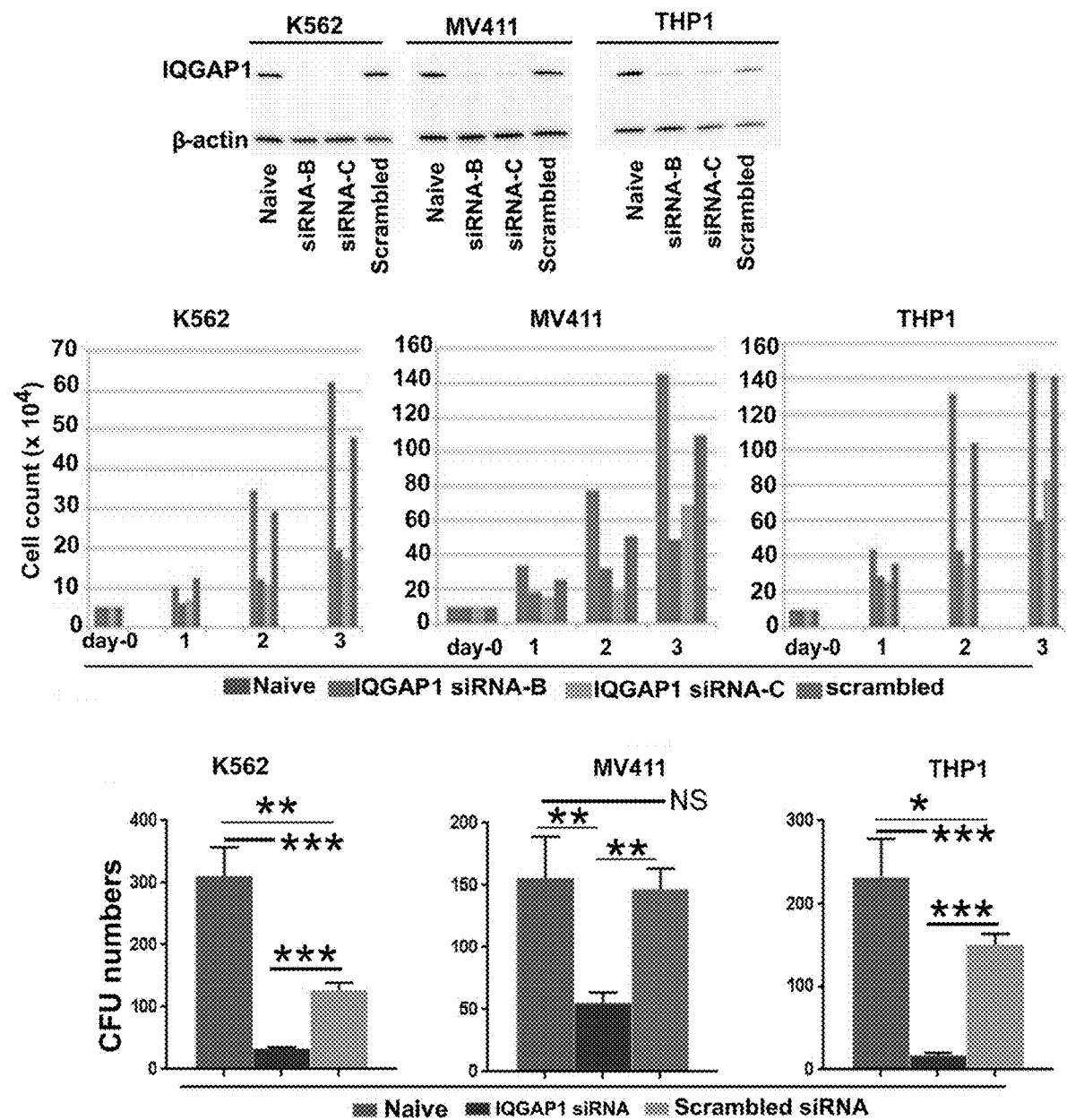
FIG. 2 depicts exemplary results demonstrating that IQGAP1 silencing via shRNA reduced proliferation and colony formation in three leukemia cell lines.

IQGAP1 silencing reduced proliferation and colony forming potential of leukemia cells: Transient IQGAP1 knockdown by two different shRNAs compared to naïve and scrambled shRNA in K562, MV411 and THP1 leukemia cells blocked the proliferation and reduced colony forming units (FIG. 2). Data shown are from one of 3 experiments, $p<0.05$.

Figure 3:
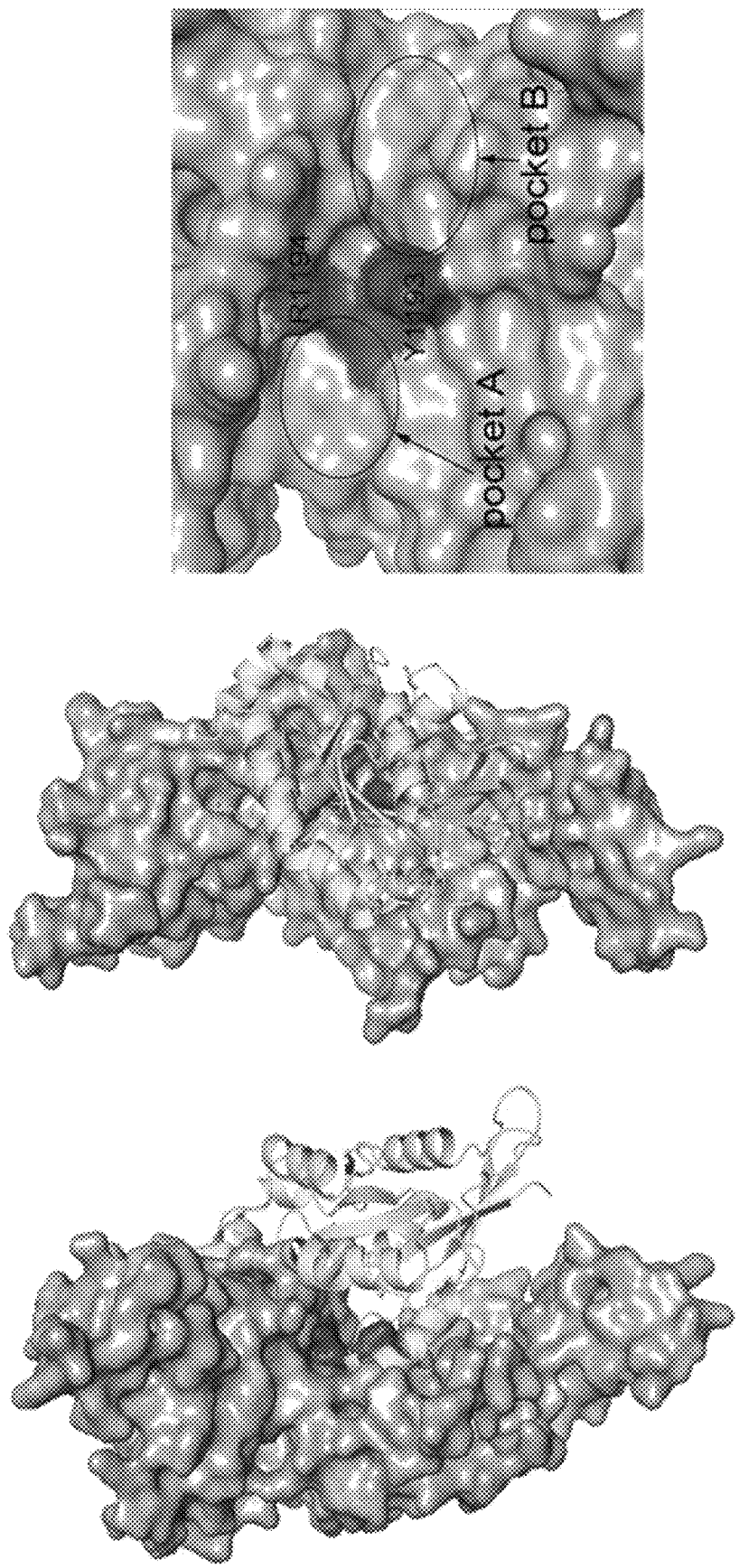
FIG. 3 depicts the predicted three-dimensional structure of GAP-related domain (GRD) of IQGAP1 in complex with Cdc42 (top left), the predicted binding interface (top right) and the four "hits" generated upon virtual screening of 212,966 molecules for predicted binding to the IQGAP1:Cdc42 interface (bottom).
Figure 3:
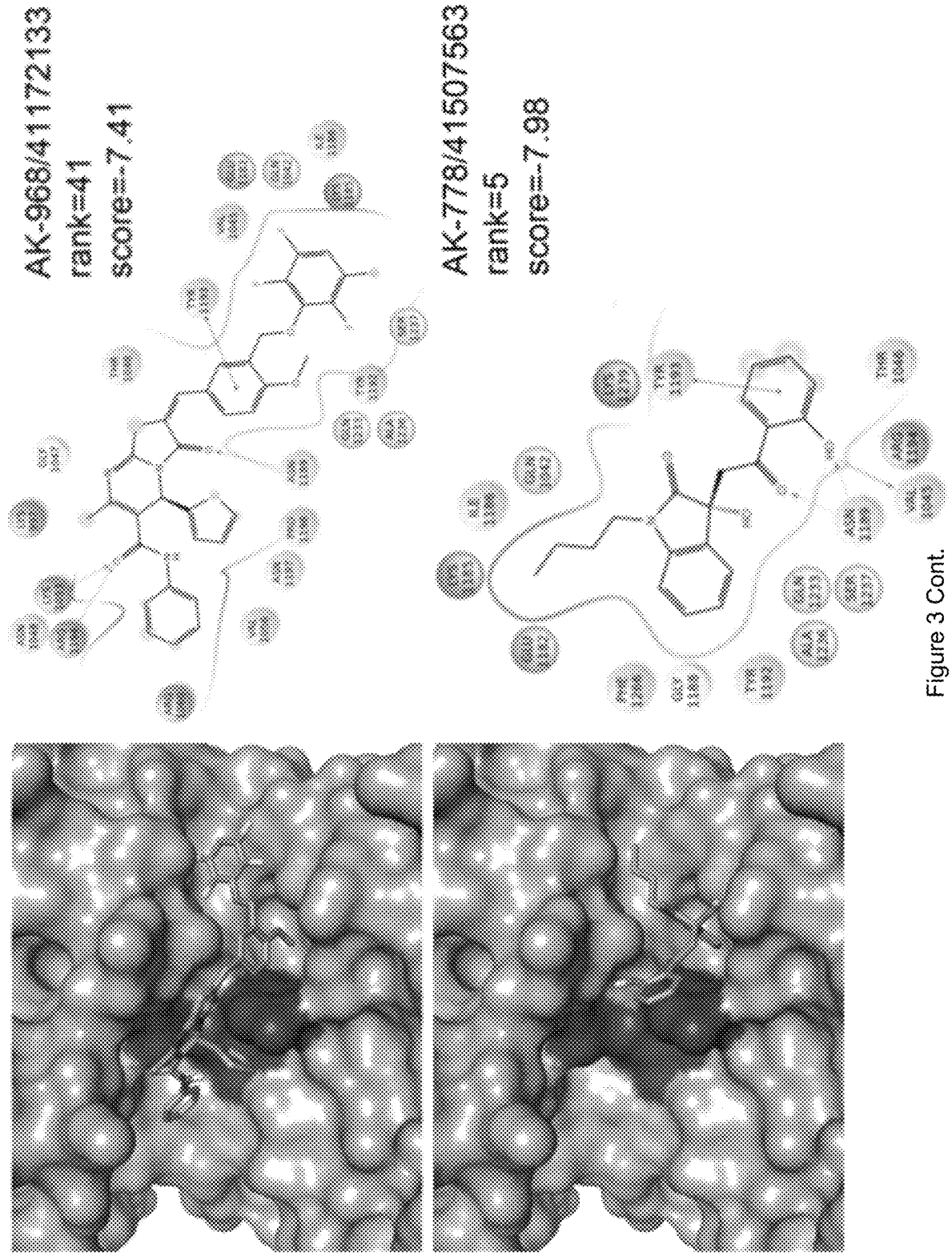
Figure 3:
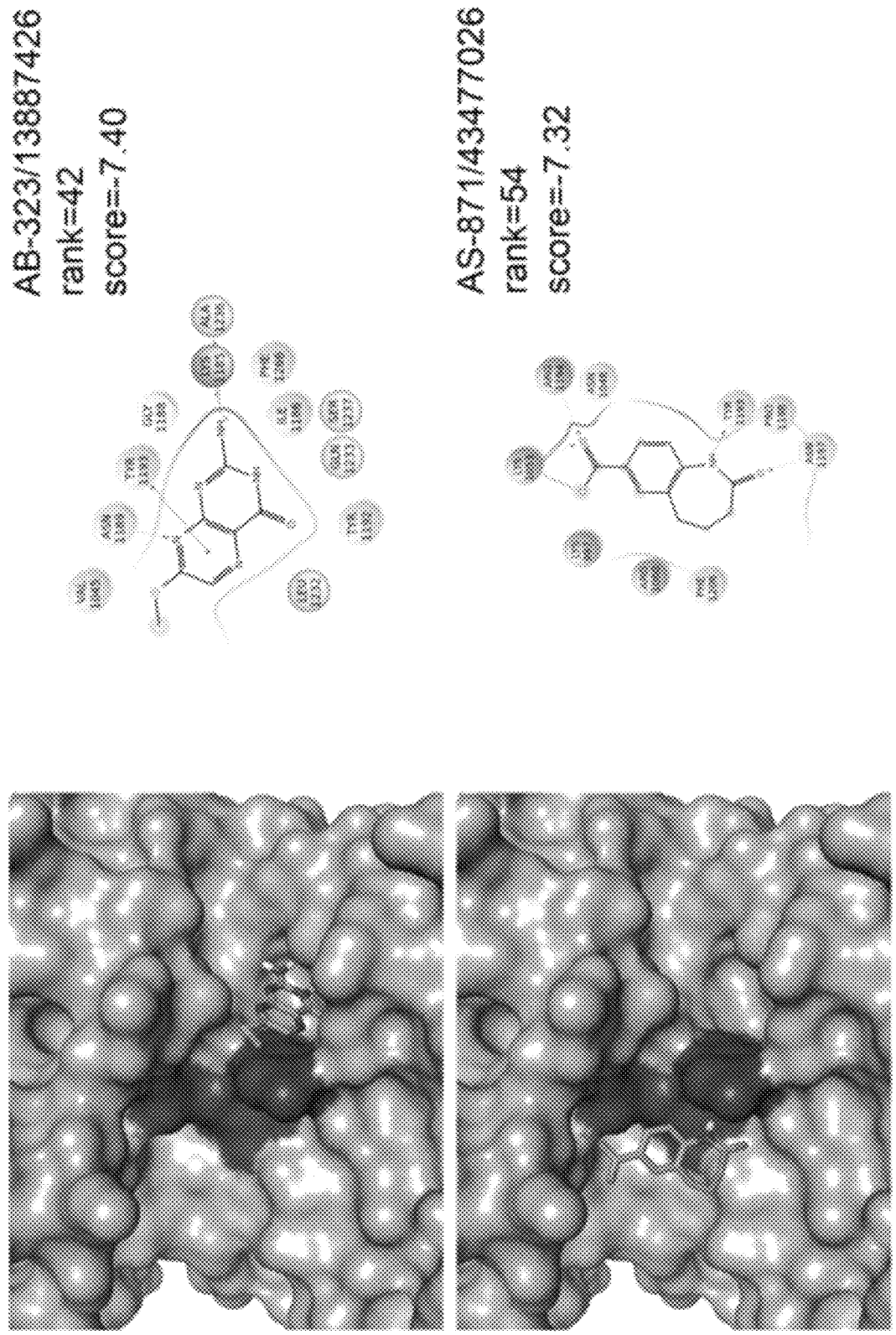

UR887Br: A novel small molecule inhibitor of IQGAP1: A virtual screening was conducted of 212,966 compounds. The exercise yielded four small molecule "hits" ranked between 5-54 based on their binding energy scores (FIG. 3). Three "hits" identified as AK778 (rank 5), AB323 (rank 42) and AS871 (rank 54) were tested for their effects on the proliferation of leukemia cell lines. The highest ranked hit (AK778) showed the most potent inhibition of AML cells in the dose range tested (data not shown). To understand the structure-activity relationship of AK778 10 close structural analogs of AK778 were obtained from a commercial vendor. Screening revealed UR778Br to be the most potent structural analog of AK778. Installation of a bromine atom on the phenyl part of the indole ring significantly enhanced the anti-proliferative activity of AK778. A limited number of analogs of UR778Br were synthesized in house to confirm the structure-activity relationship that emerged through the analog library (FIG. 5). Among the synthesized analogs, shifting the hydroxyl position on the prosthetic phenyl ring led to complete loss of activity even if the bromine on the phenyl ring was retained.

Figure 4:
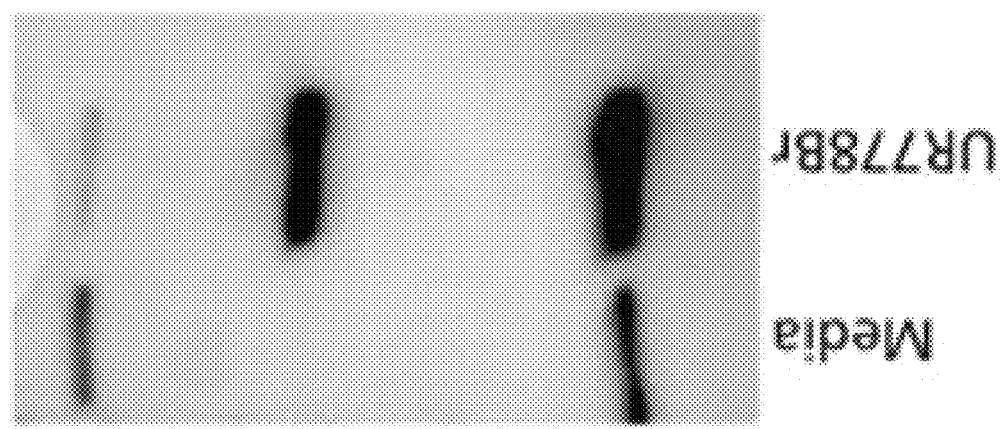
FIG. 4 depicts exemplary results demonstrating decreased expression of IQGAP1 and apoptosis of MOL13 cells in the presence of UR778Br.
Figure 9:
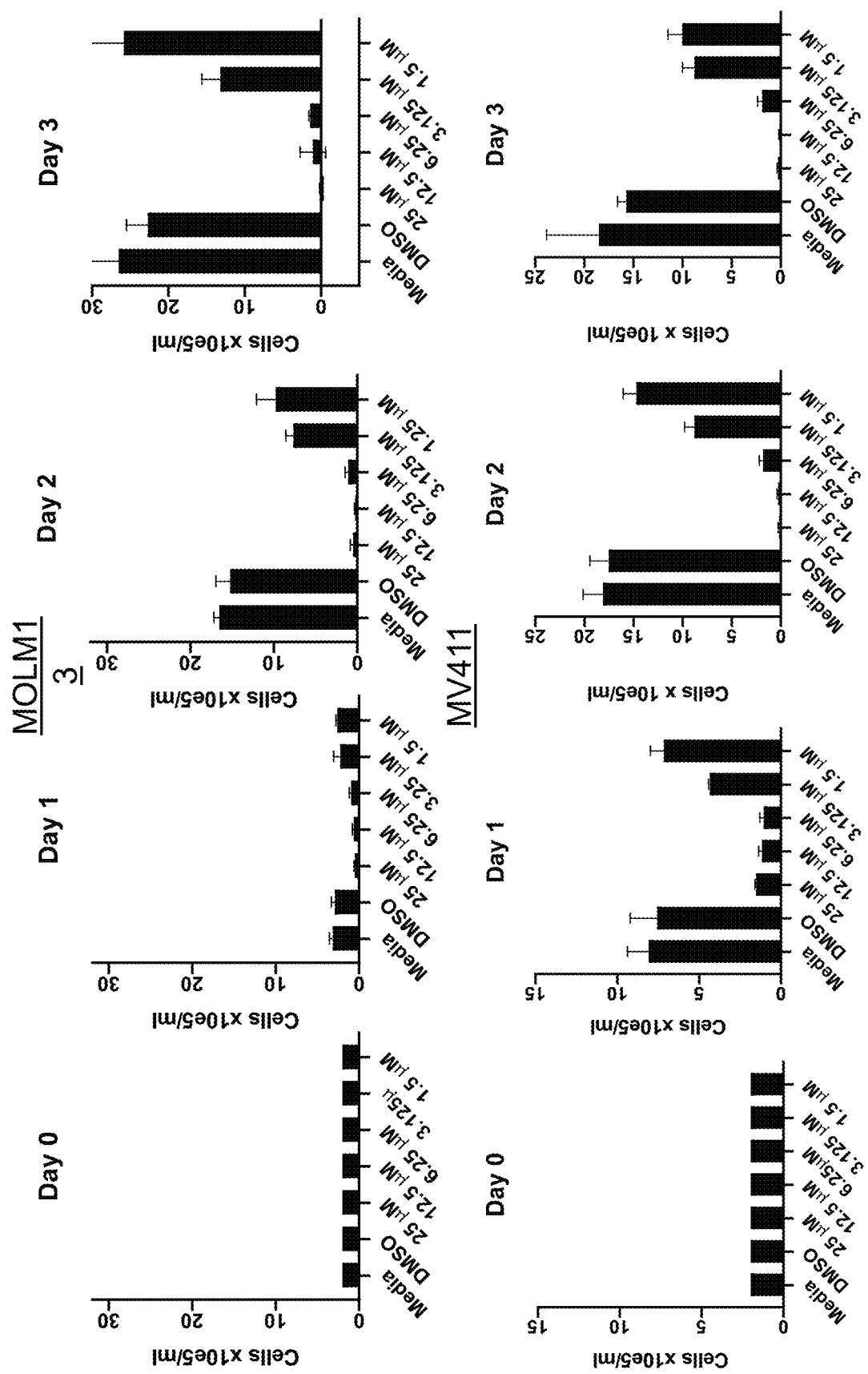
FIG. 9 depicts exemplary results demonstrating that exposure of MOLM13, MV411, THP1 and U937 leukemia cell lines to increasing concentrations of UR778Br for 72 hours resulted in dose-dependent reduction of proliferation.
Figure 9:
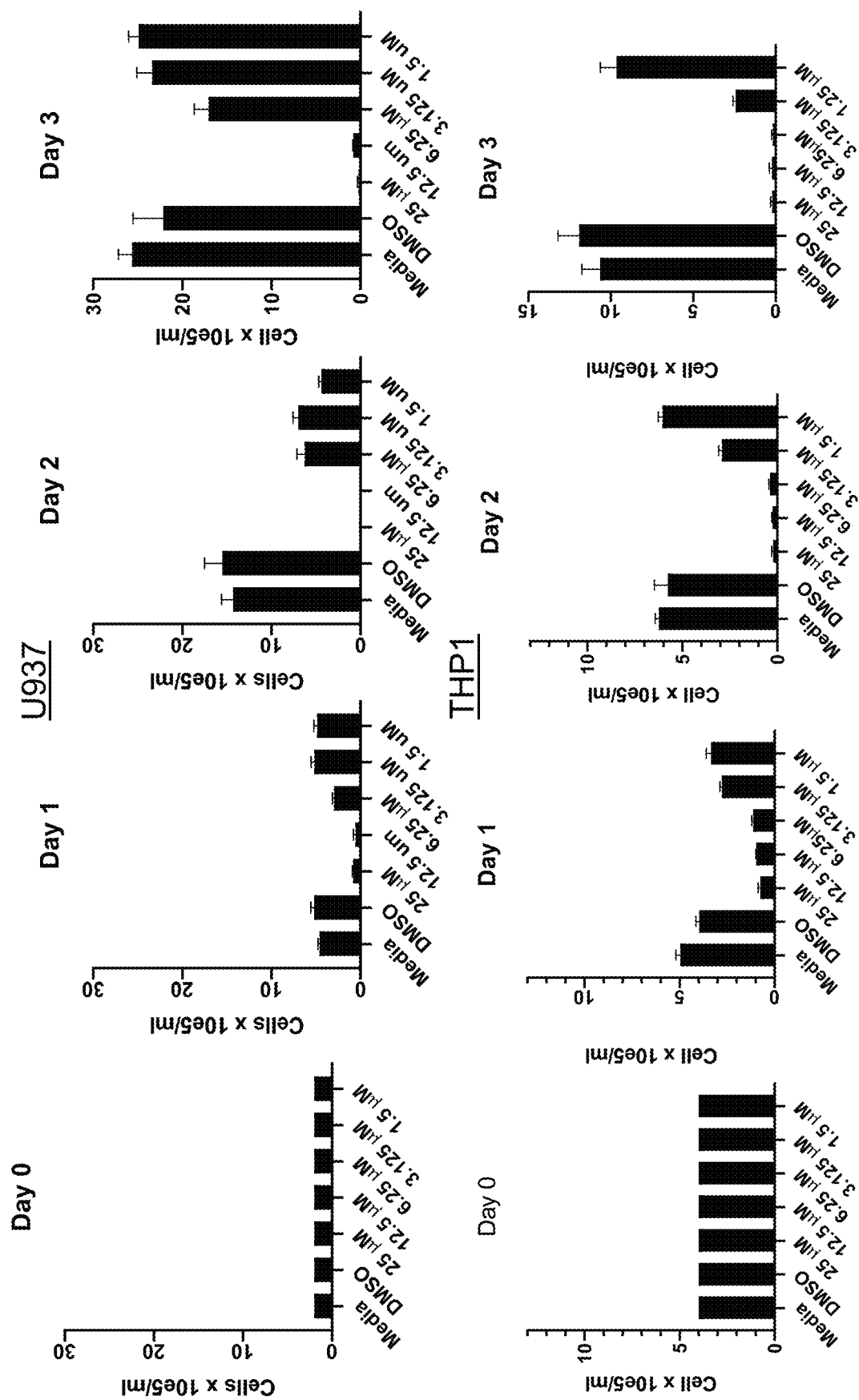
Figure 10:
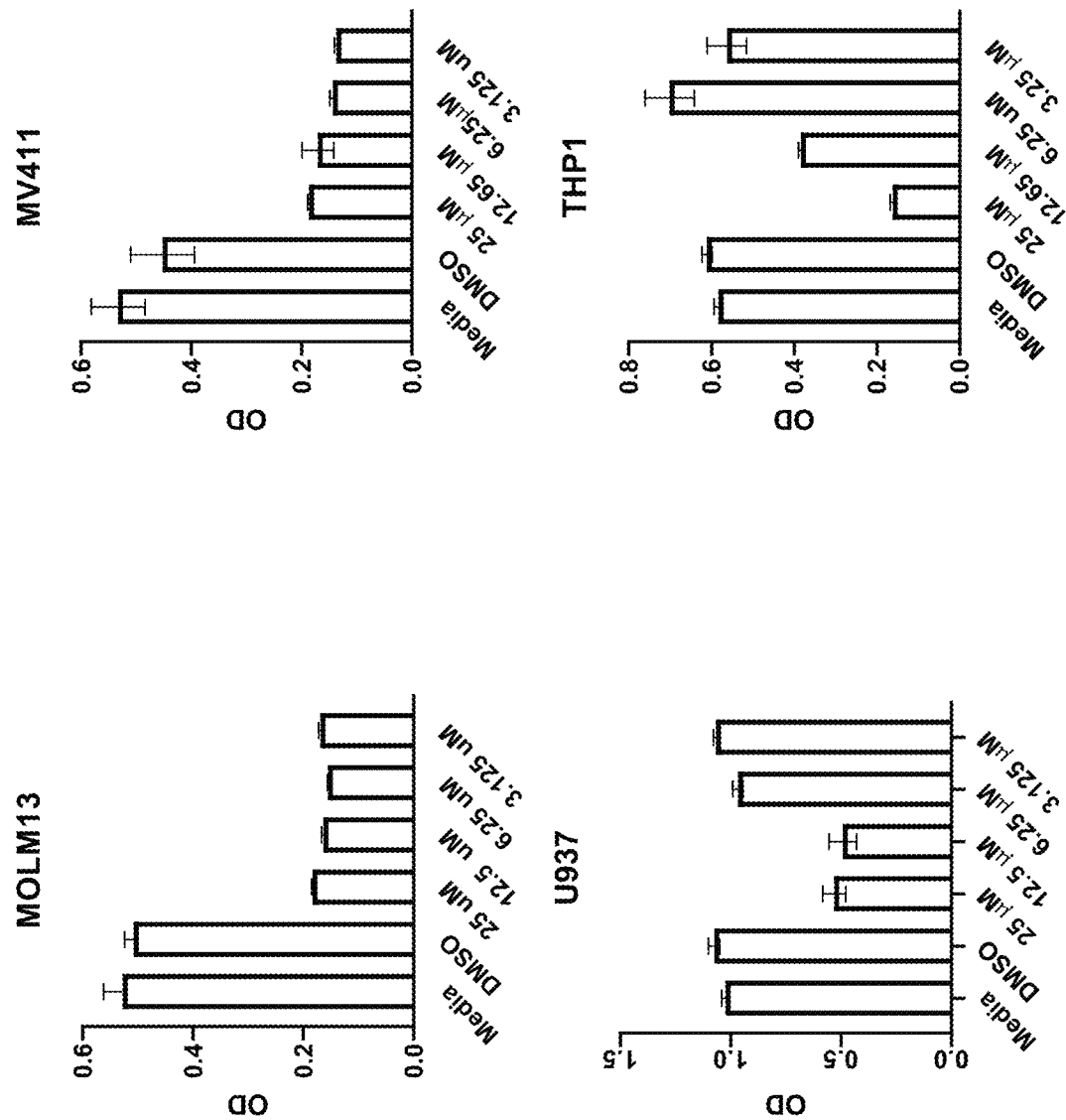
FIG. 10 depicts exemplary results demonstrating that exposure of MOLM13, MV411, THP1 and U937 leukemia cell lines to increasing concentrations of UR778Br for 48 hours results in a dose-dependent decrease in viability.
Figures 11, 11E:
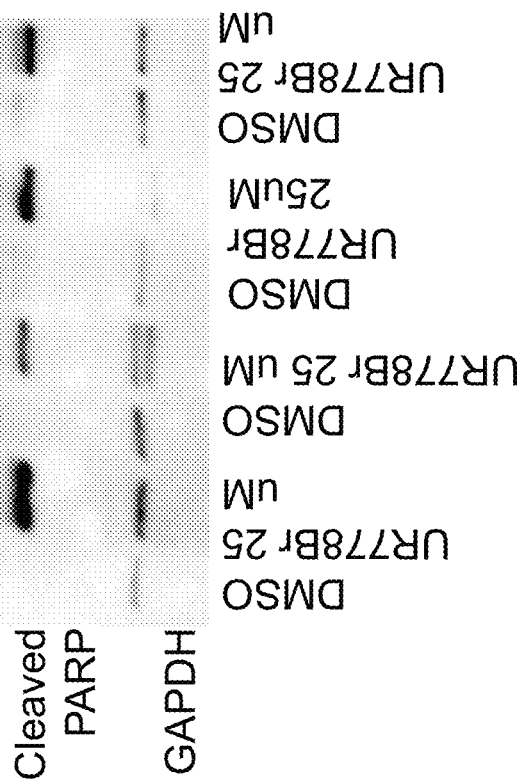

UR887Br suppressed the viability, caused cell cycle arrest and reduced IQGAP1 expression in AML cell lines. The lead compound, UR778Br decreased viability in AML cell lines in a dose-dependent fashion. While 50 µM and 25 µM had greater effect on viability data regarding its effect at 12.5 µM are shown in FIG. 10; $p<0.05$ for all cell lines as compared to DMSO control (n=3). Exposure to UR778Br for 24-hours resulted in cell cycle arrest in the G2M phase in a dose-dependent manner (FIG. 11). Exposure to 25 µM UR778Br for 24 hours resulted in decreased expression of IQGAP1 and apoptosis in MOLM13 cells (FIG. 4) Furthermore, UR778Br blocked not only proliferation (FIG. 9) but was able to suppress clonogenic progenitors as assessed by colony formation in MethoCult (Stem Cell Technologies) by MOLM13, MV411, TGHP1 and U937, at 6.25 µM concentration (FIGS. 12A-12D). In contrast UR778Br at 6.25 µM concentration did not inhibit colony formation by normal bone marrow (FIG. 11E).

Research Methods

All cell lines are available and being maintained in the investigators' lab. Effects of each new batch on viability, cell cycle and clonogenicity is performed to confirm activity.

Evaluation of the Effect of UR778Br on Primary AML Samples and Bone Marrow from Normal Donors To evaluate the effect of UR778Br on viability of normal peripheral blood mononuclear cells (PBMNC) 5 to 6 samples are studied from young samples and a similar number from older samples (over 60 years of age). Blood is drawn in heparinized tubes. PBMNCs are isolated by density centrifugation (Ficoll Hypaque, Stem Cell Technologies)). $1 \times 10^5$ PBMNCs in 50 µl media is be dispersed per well in triplicate in a 96 well plate. UR778Br is added to achieve final concentrations of 50 µM, 25 µM, 12.5 µM, 6.25 µM and 3.125 µM. Media and DMSO are added as controls. $4 \times 10^4$ MOLM13 cells per well in triplicate is be used as a positive control. At 72 hours, viability is measured by adding 20 µl of CellTiter 96 AQueous One Solution Cell Proliferation (Promega) per well followed by incubation for 4-6 hours and measurement of absorbance at 490 nM.

To evaluate the effect of UR778Br on colony formation by normal bone marrow in MethoCult bone marrow from healthy subjects collected under an approved RSRB protocol are used. Approximately 5 to 6 samples are studied from young samples and a similar number from older samples (over 60 years of age) subjects. Each experiment is repeated 3 times. De-identified cryo-preserved cells are thawed, washed and re-suspended in media. Cell count and viability are determined. Bone marrow cells are added to achieve a final concentration of $1 \times 10^5$ cells/ml of MethoCult. The following conditions are tested: media, DMSO, UR778Br 25 µM, 12.5 µM, 6.25 µM and 3.125 µM. 0.5 ml per well is dispersed in triplicate in a 24 well plate and incubated in humidified 37° C. incubator. As a positive control one of the AML cell lines is included under similar conditions. Colonies are counted at 7, 14, and 21 days.

To evaluate the effect of UR778Br on viability of primary AML cells de-identified samples of primary AML collected under RSRB approved protocols are used. Each experiment is repeated 3 times. Cryopreserved primary AML samples are thawed and re-suspended in media followed by Ficoll Hypaque separation to enrich viable cells. Between $4 \times 10^4$ to $1 \times 10^5$ cells in 50 µl is dispersed per well of 96 well plates. The following conditions are tested: media, DMSO, UR778Br 25 µM, 12.5 µM, 6.25 µM and 3.125 µM with incubation for 72 hours. Viability is estimated by adding 20 µl of CellTiter 96 AQueous One Solution Cell Proliferation (Promega) per well followed by incubation for 4-6 hours and measurement of absorbance at 490 nM. Forty-thousand MV411, MOLM13, THP1, or MOLM13 cells per well exposed to the same conditions is used as an internal control for efficacy of UR778Br.

To evaluate the effect of UR778Br on colony formation by primary AML approximately 10 samples are studied as some primary AML samples may not form colonies in vitro. De-identified primary AML cell samples previously collected and cryopreserved with subject consent on RSRB approved protocols are plated in MethoCult (Stem Cell Technologies H4435) at $1 \times 10^5$ to $3 \times 10^5$ cells/ml. Colonies are be counted after 14-21 days. When a sample that forms colonies is identified (not all AMLs are clonogenic), another aliquot is thawed and plated with media, DMSO and UR778Br in varying concentrations as described above. Colonies are counted at 7, 14 and 21 days.

Statistical analysis: In all in vitro experiments, testing in cell lines are done in at least 3 experiments, and with primary samples, experiments are repeated with 5-6 discrete normal or leukemia subjects. Data is expressed as the mean±standard error of means from the indicated number of experiments. Comparisons among different conditions (DMSO and various doses of UR778Br) are conducted using two-way analysis of variance. Student's t-test is used to test differences between groups when the data is normally distributed, or with non-parametric data, Wilcoxon rank sum testing is utilized. Statistical significance is at $p<0.05$ utilizing prism (GraphPad, La Jolla, CA, USA).

Evaluation of the Effect of UR778Br on Xenografts of Human AML in NSG Mice

Determination of antitumor activity of UR778br in an AML xenograft model is performed with mice bred, housed and handled in the Association for Assessment and Accreditation of Laboratory Animal Care-accredited animal facility. Female mice aged 8 to 10 weeks are used.

Selection of Dose of UR778Br: UR778Br is the lead small molecule. Like many lead molecules it is active in micro molar concentrations. The focus of this investigation is to ascertain/confirm its activity first and then optimize the structure such that it is effective at lower concentrations. Since PK/PD studies have not been done, there is no reliable way to estimate the dose or route of administration to achieve comparable levels of UR778Br in the tissues. As it is a small molecule, UR778Br is expected to be absorbed orally as well as via an intraperitoneal (IP) route. To start, the IP route is used due to the ease and reliability of administration. UR778Br at 10 mg/kg and 20 mg/kg daily for 5 days per week is tested for up to 6 weeks to evaluate toleration. Six NSG mice are injected with UR778Br 10 mg/kg and 20 mg/kg IP each. The mice are monitored closely and the ones that appear sick are euthanized using approved protocols. If 2 of 6 mice are euthanized, that dose of UR778Br is considered dose limiting toxicity and a lower dose is considered as MTD. If all six mice tolerate UR778Br at 20 mg/kg, the dose is not escalated further. If administering UR778Br via IP route is toxic or inactive in the initial experiment(s), it is administered by gastric lavage. The same design as described above is used to select the dose. If UR778Br at 20 mg/kg/d is well tolerated, 20 mg/kg/d and 10 mg/kg/d is used. If the MTD is lower than 20 mg/kg MTD/d and 50% of MTD/d is used. For ease of reading 20 mg/kg/d and 10 mg/kg/d have been included as the doses in the text below.

AML cell lines: Ten NOD-SCID IL-2Ry KO (NSG) mice are injected with $1 \times 10^6$ THIP1 (or U937) cells via tail vein. At 3 and 6 weeks three mice are euthanized, femurs harvested and flushed. Flow cytometry is performed on the bone marrow. Presence of 0.1% or more CD45+ cells is considered as evidence of engraftment. All mice are euthanized when sick and assessed for degree of leukemia engraftment in bone marrow and peripheral blood. GFP-transduced cell lines are used despite the ease of monitoring because immunogenicity and cytotoxicity of GFP could confound the interpretation of in vivo experimental data.

To evaluate the effect of UR778Br in vivo, twenty-five NSG mice are injected with $1 \times 10^6$ THP1 or U937 cells. Engraftment is confirmed as described above. The remaining mice (expected to be between 21 or 22) are randomly assigned to be treated with UR778Br 10 mg/kg and 20 mg/kg or vehicle IP daily. There are 6 to 8 mice per group. Following treatment, bone marrow aspirations are performed at weeks 2 and 4 and analyzed by flow cytometry for the presence and percentage of human $CD45^+$ cells. Animals are euthanized when sick. If the all vehicle treated mice are euthanized, then treated mice are also euthanized and bone marrow and blood are analyzed by morphology and flow cytometry for presence of human CD45 positive cells.

Survival for individual mice is recorded for descriptive purposes. Absence of $CD45^+$ cells is construed to indicate remission.

Primary AML: For primary patient-derived xenografts, samples are used for which there is in vitro data re susceptibility to UR778Br. Ten NSG mice are irradiated (200 rads) 24 hours before injection. Viable mononuclear cells from primary AML patients are isolated by Ficoll separation. Two-to-five-million MNCs are injected via tail vein. Starting at three weeks and weekly thereafter, bone marrow are analyzed by flow cytometry for human cell engraftment. Mice are considered to be engrafted if they have 0.1% or higher human derived $CD45^+$ cells.

Using an experimental design similar to that described above for the THP1 xenograft experiment, the engrafted mice are randomized for treatment with UR778Br at 10 mg/kg or 20 mg/kg or vehicle control IP. Following treatment, bone-marrow aspirations and flow cytometry analysis are performed at 2 and 4 weeks for human CD45 expression. Survival of individual mice is recorded for descriptive purposes. Absence of CD45 expression is construed to indicate remission. Necropsies are performed and tissues are harvested and preserved in formalin for histopathologic analysis.

If there is a strong signal in the in vivo experiments: 50% of the animals have no engraftment of leukemia and/or there is 50% prolongation in overall survival, time from engraftment to euthanasia, experiments are considered to test for statistically significant survival differences.

It is possible that primary AML cells may undergo spontaneous apoptosis over 48 to 72 hours in serum containing media. In this situation, the primary AML cells are cultured with a human bone marrow stromal cell line, HS-5 as previously described (Garrido et al., 2001, Experimental hematology 29(4): 448-457). Co-culture of primary AML cells with HS-5 cell line confers protection against spontaneous and drug-induced apoptosis. Ara-C 0.2 µM and daunorubicin 0.5 µM were added during the last 18 hours as positive controls as at those concentrations intermediate level of apoptosis were seen.

$1 \times 10^5$ cells are plated per well of a 24 well plate. Forty-eight to 72 hours later 4 to $6 \times 10^5$ viable primary AML cells are plated per well. All samples are cultured for 96 hours. Media, DMSO, UR778Br doses ranging from 25 µM to 3.125 µM are added during the last 48 hours. Ara-C and daunorubicin are added during the last 18 hours as positive controls as described above to make sure that the co-cultured with HS-5 did not render the primary AML cells impervious to the effect of drugs or small molecules in vitro. The HS-5 cell line is adherent. AML cells are harvested and viability is measured as described using the MTS agent. The effect of UR778Br on colony formation in MethoCult is measured as described above.

It is possible that UR778Br administered IP may be toxic. In this situation, UR778Br is administered via gastric lavage.

Example 2: Targeting IQGAP1-GRD Subunit Controls Growth of Human AML

AML, a clinically aggressive disease, is fatal in majority of patients (~80%) and is emerging as the leading cause of leukemia-related deaths in the US. Current therapies have plateaued in their efficacy and new therapies are urgently needed to control AML, particularly among older patients who are at the greater risk. Mortality rates from AML are rising as the population is aging.

The process of transformation and maintenance of malignant phenotype utilizes a finite number of common pathways termed hallmarks of cancer. It is hypothesized that activation of these common pathways may result in expression of antigen(s) that are shared among a spectrum of acute leukemias. To test the hypothesis, previously published experiments were replicated that had shown that immunization of rabbits with human peripheral blood WBCs that had been incubated with fluorodinitrobenzene (FDNB) elicited high titer antibodies that agglutinated a broad spectrum of human leukemia cells.

Herein it is reported that immunoaffinity purification of lysates of primary AML cells with serum from rabbits immunized with peripheral blood WBCs that had been incubated with FDNB identified the scaffolding protein IQGAP1 as part of the shared antigenic moiety. Analyses of gene expression profiles of human AML showed that IQGAP1 was overexpressed in primary human AML cells across cytogenetic subtypes compared to normal hematopoietic stem cells. shRNA knockdown of IQGAP1 in K562, MV411, and THP1 human leukemia cell lines suppressed their proliferation and colony formation potential. To develop small molecule inhibitors of IQGAP1, a virtual screening was conducted of 212,966 compounds to identify four highly ranked small molecule "hits". Further screening of the library of the highest-ranked hits yielded UR778Br that inhibited proliferation, deceased viability, caused G2/M phase arrest, resulted in apoptosis, and inhibited colony formation potential of MOLM13, MV411, THP1 and U937 human leukemia cell lines. Exposure to UR778Br also resulted in decreased viability and colony formation by primary AML samples. UR778Br did not block colony formation by bone marrow from healthy individuals in similar dose range. The data presented suggest that IQGAP1 is a therapeutic target of interest in the treatment of AML and provides the impetus for optimization and development of UR778Br and its derivatives as first in class agents in the treatment of AML.

Materials and Methods

Cell lines, cell culture and reagents: K562, MOLM13, MV411, THP1 and U937 cells were maintained in complete RPMI-1640 medium supplemented with 10% fetal calf serum, penicillin (100 units/mL), and streptomycin (100 µg/mL) at 37° C. with 5% $CO_2$ in a humidified incubator.

Immunization of Rabbits: The protocol for collecting peripheral blood samples from healthy volunteers was approved by the University of Rochester's Research Subject Review Board. De-identified samples of AML that had been collected under a protocol approved by the Research Subject Review Board were used in immunoaffinity purification experiments, Western blot- and immunohistochemical (IHC) analyses.

The research protocol for immunizing rabbits and obtaining blood samples was approved by the University of Rochester's Institutional Animal Care and Use Committee. The rabbits were housed in an AAALAC accredited vivarium overseen by the centralized Animal Resource management. The rabbit room was maintained on a 12:12 light cycle (lights on 0600), at 66.5±2° F., 30-70% humidity and experienced 10-15 air changes/hour. These environmental parameters were continuously monitored electronically and remained within NIH set points. Rabbits were housed in stainless steel and plastic molded cages providing sufficient space in compliance with Animal Welfare regulations. Rabbits received ad lib food and water during the entire study.

Rabbits were also given enrichment manipulation as described in the University of Rochester's Enrichment Plan for Laboratory Animals. Animal care technicians provided daily husbandry services and reported animal illness, injury or other abnormal behavior to the Division of Laboratory Animal Medicine (DLAM) veterinary staff. The immunization, blood draws and euthanasia of rabbits were performed as described in the IACUC protocol by NYS licensed veterinary technicians and veterinarians (DLAM).

Isolation of peripheral blood WBCs and incubation with fluoro-dinitrobenzene (FDNB): Blood from healthy volunteers was obtained under a protocol approved by the University of Rochester's IRB. The healthy subjects signed an informed consent form. Blood was drawn by venipuncture into acid citrate dextran containing tubes. It was diluted with equal volume of phosphate buffered saline, without calcium or magnesium, pH 7.2. Red blood cells were sedimented by adding 6 ml of 6% dextran (Molecular weight 500,000, cat #9605D, Lot #A84991, Research Organics, Cleveland, OH) in PBS to 40 ml of the diluted blood and incubating at room temperature for 20 minutes. The supernatant containing WBCs was aspirated and centrifuged. Contaminating RBCs were removed by hypotonic shock lysis. Cell count was determined by counting cells in a hemocytometer and viability was estimated by Trypan blue dye exclusion. Viability was in excess of 95%. 2,4-dinitrofluorobenzene (Sigma-Aldrich D1529) at 1.482 g/ml was used. As FDNB is highly reactive and photosensitive the dilutions and incubation of WBCs was carried out in glass tubes and exposure to fluorescent light was avoided. Twenty-microliters corresponding to 29.6 mg were dissolved in 2.96 ml of ethanol, yielding 10 mg/ml. One hundred and fifty-five microliters corresponding to 1.55 mg were diluted in 4.85 ml of PBS yielding 0.31 mg/ml). This solution was serially diluted to 31 picograms/ml. Based on Avogadro's number this concentration corresponds to $1\times10^{11}$ molecules per ml. WBCs at $1\times10^7$ cells per ml were mixed with equal volume of FDNB at 31 picograms corresponding to $1\times10^{11}$ molecules per ml, yielding an average of $1\times10^4$ molecules per cell. The cells were incubated for 12 to 15 minutes at RT, washed, resuspended in ice cold PBS, counted and $1\times10^7$ cells were injected subcutaneously, once per week for 16 weeks in three rabbits. A rabbit was injected with equal number of unmodified WBCs subcutaneously once per week for 16 weeks as the control. At week 16 blood samples were collected by venipuncture, serum separated, complement was inactivated, and the sera were absorbed against pooled unmodified WBCs from normal healthy volunteers at 37° C. for 1 hour. The absorbed sera were centrifuged and aliquots and stored at −80° C. After confirming presence of an immune response, the rabbits were euthanized by a veterinarian as described in the IACUC protocol. Sera were separated, complement inactivated by heating the sera at 56° C. for 60 minutes, absorbed against pooled unmodified WBCs from normal healthy volunteers at 37° C. for 1 hour. Aliquots stored at −80° C. To confirm elicitation of an immune response sera were tested by flow cytometry using KG1 alpha, K562 and MV411 (LSR; Becton Dickinson).

Figure 6A:
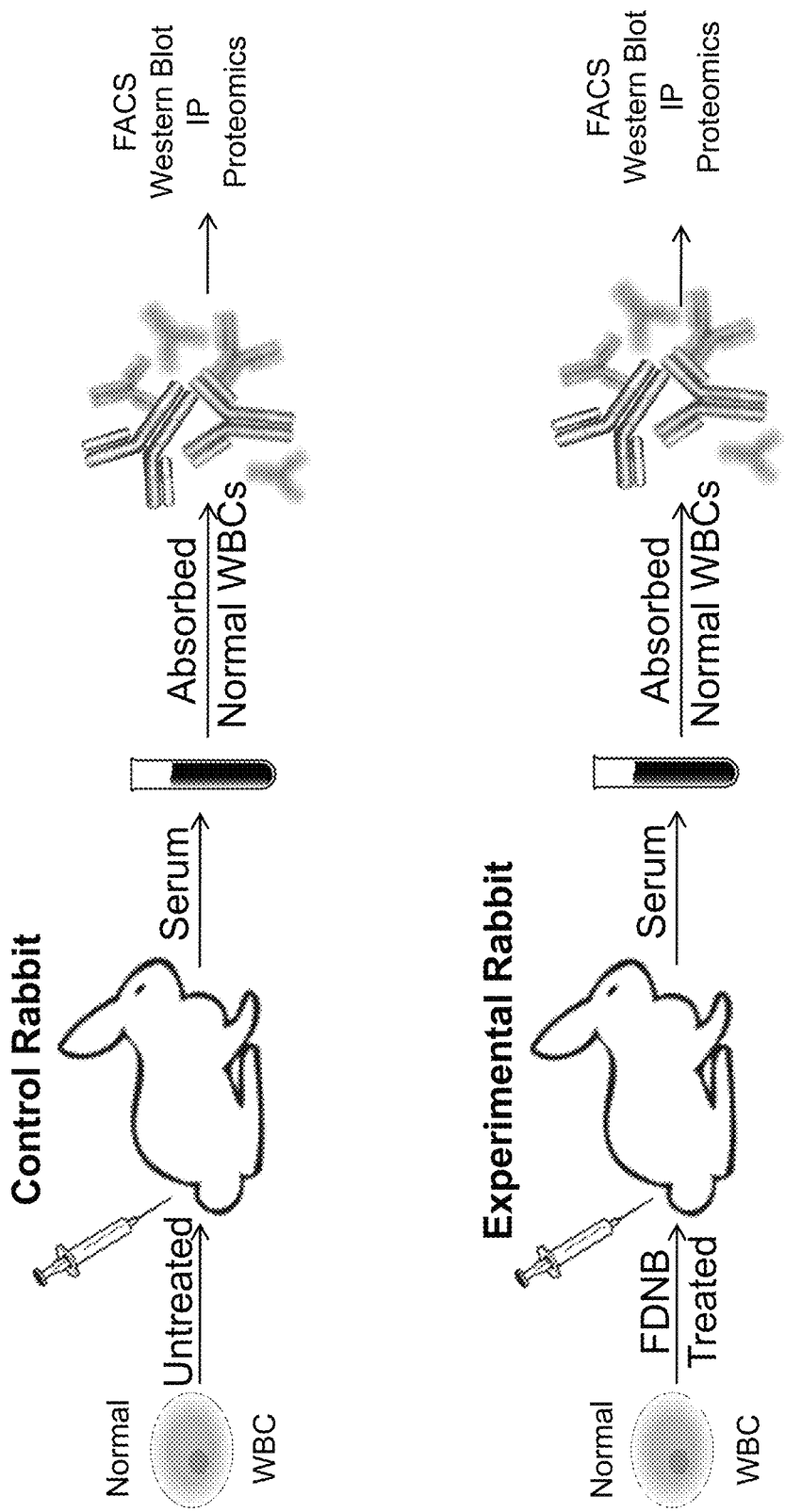
FIGS. 6A through 6E depict exemplary results demonstrating that IQGAP1 is overexpressed in AML.
Figure 6B:
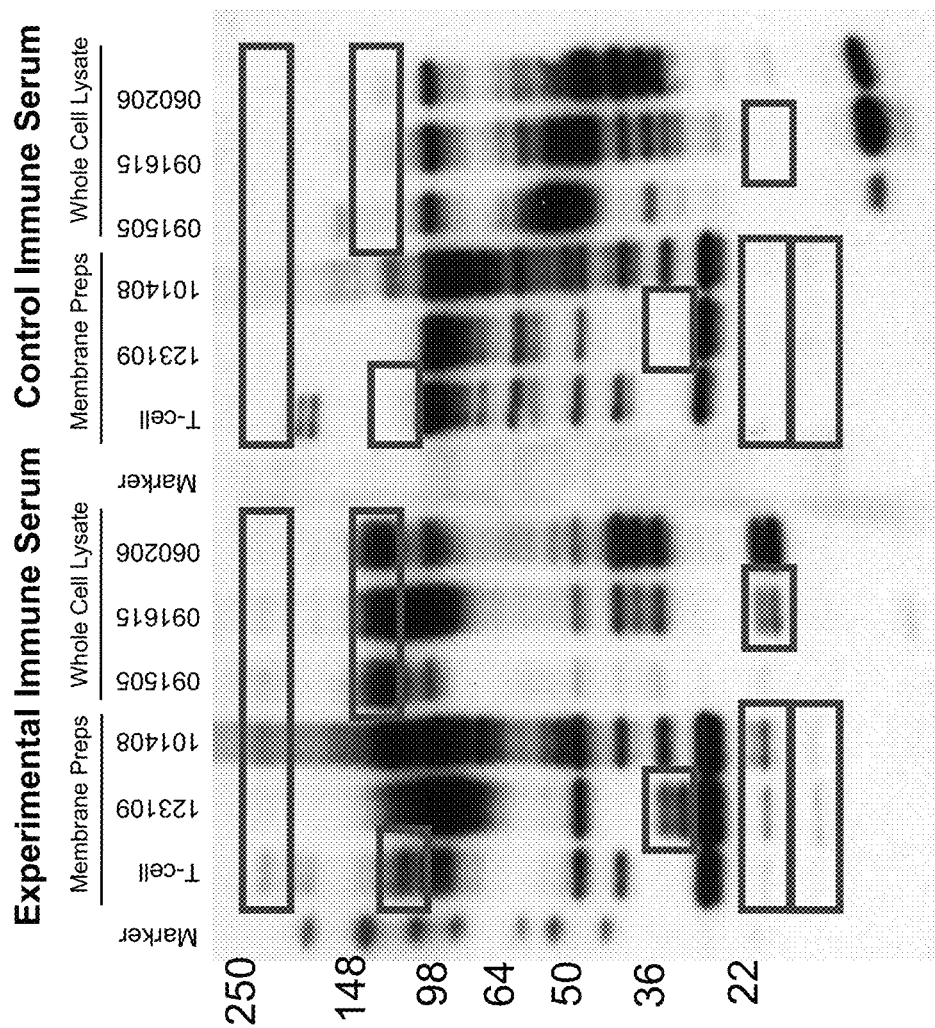
Figure 6C:
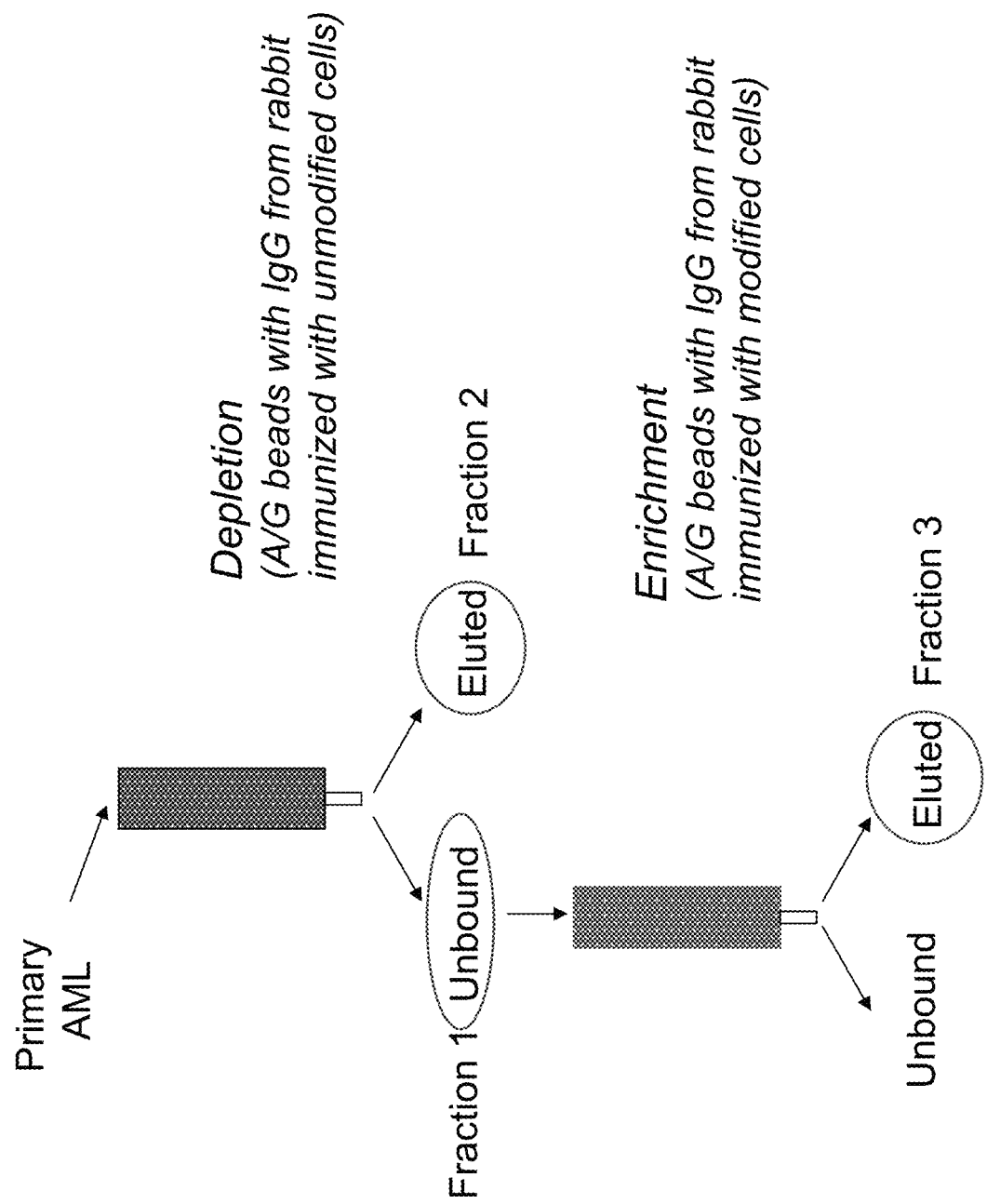

Immunoaffinity Purification: Protein A/G PLUS Agarose Beads (Santa Cruz Biotechnologies (sc-2003)) were used per manufacturer's instructions. A strategy of depletion followed by enrichment was adopted as shown in FIG. 6C. Cell pellets were lysed in radioimmunoprecipitation (RIPA) buffer (50 mM Tris-HCl, pH 7.5, 150 mM NaCl, 1% deoxycholic acid, 1% Triton X-100, 0.25 mM EDTA, and 5 mM sodium fluoride) to which Halt Protease and Phosphatase inhibitor cocktail, Thermo Scientific, was added. One hundred microliters of the lysis buffer were added per million cells. The pellet was disaggregated by passing through a 21 G needle×5. Incubated on ice for 15 minutes, centrifuged at 13000 rpm for 10 minutes. Protein concentration was measured using Piercenet BCA using manufacturer's instruction.

Whole cell lysates of de-identified clinical AML samples were incubated with protein A/G agarose beads to which IgG from the rabbit immunized with unmodified WBCs was attached. An aliquot of the unbound fraction was set aside for protein estimation, Western blot and for IP. The remainder of the unbound fraction was incubated overnight at 4 C with protein A/G agarose beads to which IgG from rabbits immunized with WBCs modified by FDNB was attached. An aliquot of the unbound fraction was set aside for protein estimation, Western blot and for IP. Antigens bound to agarose beads were eluted by boiling the beads.

Proteomic analysis: For LC-MS/MS analysis the three samples: index-, affinity purified- or depleted protein samples were cleaned up for lipid and detergent removal by a 10-minute electrophoresis step on SDS-PAGE. The gel was stained with Coomassie blue and the gel portions were isolated, processed for trypsin digestion and LC-MS/MS analysis. In brief, gel pieces were diced into 1-mm squares, rinsed with water and 50 mM ammonium bicarbonate buffer, and dehydrated. Reduction of disulfide bonds was conducted with 10 mM dithiothreitol, followed by alkylation with 50 mM iodoacetamide. Proteins were digested by rehydrating the gel slices in 20 μg/ml trypsin (Promega) in ammonium bicarbonate buffer plus 10% acetonitrile for 1 h at 24° C., followed by overnight incubation at 37° C. and a second addition of trypsin the next day for 3 hours. The digested material was extracted from the gel, combined, and dried, using a vacuum concentrator. 10-20% of the digest was loaded on a Magic C18 AQ (Michrom) Nano spray column/tip on a Thermo LTQ mass spectrometer and washed with 5% methanol, 0.1% formic acid for 10 min before peptide elution began, using a 5-60% methanol gradient. The LTQ ion trap mass spectrometer, equipped with a nano electrospray ionization source, ran a full MS survey scan every 3 seconds in the data-dependent mode to collect seven MS/MS fragmentation spectrum per cycle, using dynamic exclusion to access lower intensity peptides. The raw data files containing MS and fragmentation spectrum data used in a Mascot search, against the complete human and rabbit proteomes. Mascot (Matrix Sciences) search parameters included precursor and fragment ion mass tolerance of 1.5 and 0.8 Daltons, respectively, one 13C incorporation, one missed trypsin cleavage site, fixed carbamidomethyl-cysteine modification, and variable methionine oxidation. Mascot search results files were uploaded into Scaffold (Proteome Software) and additionally searched with X!Tandem in the Scaffold environment. Threshold values for protein identification were 95% minimum protein identification probability, with 90% peptide probability. Relative abundance of a protein in different samples was semi-quantitatively determined, using spectral counting analysis.

Antibodies used: Anti-IQGAP1 murine monoclonal (D3): sc-374307 (Santa Cruz Biotechnology, Inc.), anti-IQGAP1 rabbit monoclonal D6E3J (Cell Signaling; 290165), anti-GAPDH rabbit monoclonal 14C10 (Cell Signaling), anti-α tubulin rabbit monoclonal 11H10 (Cell Signaling), anti-Cdc42 murine monoclonal antibody (#ACD0#) Cytoskeleton, anti-cleaved PARP (Asp214) rabbit monoclonal antibody #5625 (Cell Signaling), HRP-conjugated anti-rabbit antibody #7074 (Cell Signaling), and HRP-conjugated anti-mouse antibody #7076 (Cell Signaling).

Western Blot Analysis of AML patient cells: De-identified clinical AML samples collected under an IRB-approved protocol were used for Western blot and immunoaffinity purification. An aliquot of the lysate was mixed with equal volume of 2× Laemmle buffer plus 2 beta-mercaptoethanol, boiled for 10 minutes and then stored at −20° C. The samples were electrophoresed in 10% tris-glycine gels (Bio-Rad), resolved proteins were transferred to PVDF membrane (Immobilon, Millipore), blocked with 5% dry milk in tris-buffered saline with 0.05% Tween (TBS-T) for 1 hour at room temperature, and probed with immune sera from the rabbits at 1:5000 dilution at 4° C. overnight. The primary antibody was poured off, the membrane was washed with TBST×3. Horseradish peroxidase conjugated anti-rabbit antibody (Cell Signaling) and Amersham ECL Prime reagent (GE Healthcare Biosciences) or Super Signal West Femto Maximum Sensitivity Substrate, (34095; Thermo Scientific) were used. The blots were read using BioRad ChemiDoc MP Imaging System and analyzed with the provided software.

IQGAP1 Expression in AML patient samples: To determine the expression of IQGAP1 in a larger sample the raw data from the publication by Gentles et al. (JAMA, 2010, 304(24):2706-15) were downloaded from the Gene Expression Omnibus (GEO) at the National Center for Biotechnology Information (NCBI) and is available under accession number GSE24006. Data analysis was carried out using Partek Genomic Suite (Partek Inc. Saint Louis, MO). Chips were normalized using Robust Multi-array Average (RMA) and a one-way ANOVA was conducted to interrogate significance on the IQGAP probe set "213446_s_at."

shRNA Mediated Knockdown of IQGAP1: IQGAP1 shRNA cloning and lentivirus production were performed as previously described (Ashton J M, et al., Cell stem cell, 2012, 11:359-372). Briefly, each pLKO.1-shRNA construct was co-transfected with pPax2 (provides packaging proteins) and pMD2.G (provides VSV-g envelope protein) plasmids into 293T cells (System Bioscience) to produce lentiviral particles. At about 48 hours post transfection, 293T culture supernatants containing lentivirus particles were harvested, filtered, aliquoted and stored in −80° C. freezer for future use. At the day of infection, these lentivirus aliquots were thawed and used to infect leukemia cells lines (K652, MV411 and THP1 cells). Cells were typically infected by mixing 1×10⁶ cells in 0.5 ml MOLM-13 media with 0.1 ml of freshly thawed lentivirus and Polybrene at a final concentration of 10 μg/ml. At 3-4 days post infection the cells were analyzed by flow cytometry. Greater than 95% of cells were GFP-positive. Therefore, cells were analyzed by western blotting for the knockdown efficiency of IQGAP1.

shRNA targeting sequences used for IQGAP1 are listed below:

```
                                    (SEQ ID NO: 1)
sh-Scrambled Control:    CCTAAGGTTAAGTCGCCCTCG (SEQ ID NO: 2)
sh-IQGAP1-Clone B:       GCATCCACTTACCAGGATATA (SEQ ID NO: 3)
sh-IQGAP1-Clone C:       GCAGCTCCTGAGTGATAAACA
```

Proliferation: To measure proliferation K562, MV411 and THP1, naive cells and cells transfected with two different shRNA targeting IQGAP1 as well as transfected with scrambled shRNA were dispersed in 48-well plates at 50000 cells per ml at 37° C. with 5% $CO_2$ in a humidified incubator. Cell counts were done using a hemocytometer at 24-, 48- and 72 hours. Each experiment was repeated three times.

Colony forming unit assay: To evaluate the effect of knocking down expression of IQGAP1 on clonogenicity of K562, MV411 and THP1, naïve cells, and cells transfected with one of the two shRNAs that had knocked down expression of IQGAP1 and or cells transfected with scrambled shRNA were added to MethoCult H4435 Enriched (Stem Cell Technologies, catalog number 04435), to achieve concentrations of 2000 cells/ml, 500 cells/ml and 200 cells/ml. Each condition was done in triplicate or quadruplicate. The plates were at 37° C. with 5% $CO_2$ in a humidified incubator. Colonies were counted at 7 and 14 days and sometimes and 21 days.

Immunohistochemical analysis of leukemia cells lines and primary AML: De-identified bone marrow biopsy material containing AML was randomly selected from pathology archives and individual cases were selected based on number and abundance of diagnostic cells. Formalin fixed paraffin embedded tissue sections were cut at 4 microns and mounted on glass slides and baked for one hour at 60° C. to assist in tissue adhesion to the slide. Slides were then deparaffinized through xylene and graded alcohols followed by a brief rinse in wash buffer. Pretreatment of the slides was performed in a pressure cooker using a pH=6 buffer for 20 minutes at 99° C., with a brief cool down period. Slides were incubated with primary antibody (Anti-IQGAP1 murine monoclonal (D3): sc-374307; Santa Cruz Biotechnology, Inc.) diluted to 1:100 for 60 minutes at room temperature. Development of the antibody was performed using the Flex HRP with DAB kit from Dako (Agilent Technologies) and hematoxylin counterstain.

IQGAP1 mRNA expression in primary human AML and normal HSC controls: BloodSpot is a curated publicly available gene expression dataset. AML samples came from the Microarray Innovations in Leukemia study headed by the European Leukemia Network and sponsored by Roche Molecular Systems, Inc. The normal hematopoietic subsets were from multiple studies. (http://servers.binf.ku.dk/bloodspot/). The expression of IQGAP1 in primary human AML across cytogenetic subtypes was compared to normal HSC controls.

Virtual screening: The complex structure of Ras/GAP-334 with PDB code of 1WQ1 was used to obtain the relative position of GRD and Cdc42. Specifically, the structures of GRD (PDB code 3fay) and Cdc42 (PDB code 1AN0) were superimposed onto GAP-334 and Ras, respectively. The binding model of GRD with Cdc42 is shown in FIG. 3. The conserved motif 1192YYR1194 was located inside the protein binding interface. T1046 positioned nearby the GDP from Cdc42, which is consistent with the model build in the literature (DOI: 10.1074/jbc.M808974200). The region around 1192YYR1194 was chosen as binding site for virtual screening. The 3D protein structure file (.pdb) was retrieved from the Protein Data Bank (PDB) with the accession code 3fay. Water molecules as well as other irrelevant ligands were removed from the pdb file, while hydrogen atoms were added to the protein. Energy minimization was done to remove the clashes. The SD file of specs compounds were downloaded from website www.specs.net. Molecular weight filter was used to keep the molecules within 100-800. The molecules were then converted from 2D to 3D structure and energy minimized using OpenBabel 2.3.0. Virtual screening was performed by using AutoDock Vina. Receptor and ligands were prepared using MGLTools 1.5.6. Polar hydrogen atoms were added and gasteiger charges were assigned for all the ligands. AutoDock generates different ligand conformers using a Lamarckian genetic algorithm (LGA). The center of the grid box was set to the center of R1194. The box size was set to 80×80×80 with grid spacing 0.375 Å in each dimension, which is large enough for the free rotation of the ligand. All the other parameters were kept as default. The compounds from specs.net (www.specs.net) were used as ligands in the virtual screening. Only molecules with molecular weight larger than 100- and less than 800 gm/mol were used. Totally 212,966 molecules entered the virtual screening experiment. UR778Br was purchased from Toronto Research Chemicals Effect of UR778Br on proliferation of cell lines: Proliferation of MOLM13, MV411, THP1 and U937 cells was measured by counting cells in a hemocytometer. Briefly, cells were seeded at 20,000 to 40,000 cells/well in triplicate wells of a 96 well plate and treated with a range of UR778Br doses and incubated at 37° C. with 5% $CO_2$ in a humidified incubator. Cell counts were determined at 24-, 48- and 72 hours.

Effect of UR778Br on viability of cell lines: Viability of MOLM13, MV411, THIP1 and U937 was determined by the MTS assay. Briefly, 20,000 to 40,000 cells/well were seeded in triplicate wells of a 96 well plate and treated with a range of UR778Br doses and incubated for 48 to 72 hours at 37° C. with 5% $CO_2$ in a humidified incubator. Cell Titre96R Aqueous One Solution Cell Proliferation Assay reagent (Promega Corp., catalog number: G3580) diluted 1-10 in complete RPMI medium was added and cells were incubated for 4 hours. The optical density (OD) values were read at 490 nM wavelength using BioRad iMark microplate reader. Experiments were performed in triplicates; data are expressed as the mean of the triplicate determinations (X±SD) of a representative experiment in % of absorbance by samples with untreated cells [=100%].

Cell cycle analysis: For cell cycle analysis, Leukemia cell lines were washed with 1× phosphate buffered saline (PBS Mediatech, Inc., Manassas, VA, USA) and centrifuged at 1200 rpm for 8 minutes. Cell pellet was re-suspended in 100 microliters of Cytofix/Cytoperm™ (BD Biosciences, Cat No. 554722) buffer for at room temperature (RT) for 15 minutes. Cell suspension washed with 1×PBS and centrifuged at 1200 rpm for 8 minutes and re-suspended in 1 ml of culture media containing 1 µl of Vybrant® DyeCycler™ Violet Stain (ThermoFisher Scientific, Cat No. V35003). Cell suspensions were incubated at 37° C. in a 5% $CO_2$ incubator for least 30 minutes. Cell suspensions were analyzed using a LSRII™ flow cytometer (BD Biosciences, San Jose, CA, USA). A minimum of 8,000 cells were included in the analysis of each sample. Data were analyzed by FlowJo software (Tree Star, Ashland, OR, USA) and collected on linear scale for forward and side scatter (i.e., FSC and SSC, respectively) and on a linear scale for violet fluorescence channel minutes.

Effect of UR778Br on apoptosis in primary AML cells: Primary AML cells were treated with DMSO or varying concentrations of UR778Br and cytarabine 5 µM and cultured in a 37° C., 5% $CO_2$ incubator for 24 and 48 hours. The cells were stained for 15 min in annexin-V binding buffer (10 mM HEPES/NaOH, pH 7.4, 140 mM NaCl, 2.5 mM $CaCl_2$)) containing annexin-V-APC antibody (BD Biosciences) and DAPI (Sigma). Stained cells were analyzed immediately on using a LSRII™ flow cytometer (BD Biosciences, San Jose, CA, USA).

For measurement of apoptosis by Western blot the MOLM13, MV41, THP1 and U937 cells treated with UR778Br for 24 hours were lysed and expression of cleaved PARP, an indicator of apoptosis, was measured as described above.

Effect of UR778Br on colony formation cell lines: MOLM13, MV411, THP1 and U937 were added to MethoCult H4435 Enriched (Stem Cell Technologies, catalog number 04435) to achieve concentration of 2000 cells/ml, 500 cells/ml and 200 cells/ml. UR778br was added to achieve a range of concentrations. Each condition was done in triplicate. The plates were incubated at 37° C. with 5% $CO_2$ in a humidified incubator Colonies were counted at 7, 14 and 21 days.

Effect of UR778Br on colony formation by normal bone marrow: Vials of cryopreserved aliquots were thawed the in a 37° C. water bath. Nine ml of RPMI with 2% FBS were added dropwise to the cells in 1 ml of freezing media, centrifuged at 1000 rpm for 5 min and re-suspended in 5 ml of RPMI. The cells were counted in a hemocytometer and viability estimated by Trypan blue dye exclusion. The cells were added to MethoCult H4435 Enriched (Stem Cell Technologies, catalog number 04435) to achieve concentrations of $5×10^4$ to $1×10^5$ viable cells/ml. UR778Br was added at indicated concentrations. The mixture was vortexed and allowed to settle. Each condition was dispersed in triplicate or quadruplicate. The plates were incubated at 37° C. with 5% $CO_2$ in a humidified incubator and colonies were counted at 7, 14 and 21 days. Images of colony forming unit assays were acquired using the Celligo imaging cytometer (Nexcelom Biosciences) at a resolution of 1 pixel/µm. Celligo instrument software was used for image processing.

Effect of UR778Br on viability of primary human AML cells: Vials of primary AML cells cryopreserved in liquid nitrogen were thawed rapidly in a 37° C. water bath. The contents, generally one ml, were transferred to a 15 ml conical tube, one tenth the volume of DNase was added (bovine pancreas deoxyribonuclease, Sigma Aldrich D4263-5VL), it was mixed gently and incubated in a 37° C. water bath for 90 seconds. 9 ml of DMEM with 2% FBS was added dropwise and mixed gently. Samples were then centrifuged for 5 to 6 minutes, aspirated and the supernatant discarded. 70 µl of DNase were added and mixed gently. 10 ml of DMEM with 2% FBS was added slowly to resuspend and then the sample was centrifuged for 5 to 6 minutes. Supernatant was discarded, 50 µl of DNase was added, sample was mixed gently and the pellet was resuspended in 5 ml of IMDM+10% FBS, L-glutamine 2 mM (GIBCO) and penicillin and streptomycin (50 units and 50 mcg/ml). The cells were counted in a hemocytometer with viability estimated by Trypan blue dye exclusion.

Primary cells were cultured in 37° C., 5% $CO_2$ incubator. DMSO, UR778 over a range of concentrations and cytarabine 5 micromolar were added. After incubation for 24 and 48 hours the cells were stained for 15 min in annexin-V binding buffer (10 mM HEPES/NaOH, pH 7.4, 140 mM NaCl, 2.5 mM $CaCl_2$)) containing annexin-V-APC antibody (BD Biosciences) and DAPI (Sigma). Stained cells were analyzed immediately on BD FACS Celesta, flow cytometer (BD Biosciences). Viable cells were scored as annexin-V and DAPI double negative cells.

Effect of UR778Br on clonogenicity of primary AML cells: Vials of primary AML cells cryopreserved in liquid nitrogen were thawed rapidly in a 37° C. water bath. The contents, generally one ml, were transferred to a 15 ml conical tube, one tenth the volume of DNase was added (bovine pancreas deoxyribonuclease, Sigma Aldrich D4263-5VL), it was mixed gently and incubated in a 37° C. water bath for 90 seconds. 9 ml of DMEM with 2% FBS was added dropwise and mixed gently. Samples were then centrifuged for 5 to 6 minutes, aspirated and the supernatant discarded. 70 µl of DNase were added and mixed gently. 10 ml of DMEM with 2% FBS was added slowly to resuspend and then the sample was centrifuged for 5 to 6 minutes. Supernatant was discarded, 50 µl of DNase was added, sample was mixed gently and the pellet was resuspended in 5 ml of IMDM+10% FBS, L-glutamine 2 mM (GIBCO) and penicillin and streptomycin (50 units and 50 mcg/ml). The cells were counted in a hemocytometer with viability estimated by Trypan blue dye exclusion.

The cell suspension was then added to MethoCult Enriched H4435 (Stem Cell Technologies, catalog number 04435) to achieve a final concentration between $5 \times 10^4$ to $2 \times 10^5$/ml. DMSO, UR778Br or cytarabine were added to achieve indicated concentrations. The mixture was vortexed and allowed to settle. Each condition was dispersed in quadruplicate, 0.5 ml/well of a four well plate (Nunclon, Thermo Scientific). The plates were incubated 37° C., 5% $CO_2$ incubator and colonies were counted at 7, 14 and 21 days. Images of colony forming unit assays were acquired using the Celligo imaging cytometer (Nexcelom Biosciences) at a resolution of 1 pixel/µm. Celligo instrument software was used for image processing.

Measuring activation of Cdc42: To measure the amount of activated Cdc42 upon exposure to FDNB in WBCs from normal/healthy volunteers, a Cdc42 pull-down activation assay was used (catalog BK034-S, from Cytoskeleton, Inc. 1830 S. Acoma St, Denver, CO 80223). The assay uses the Cdc42/Rac Interactive Binding (CRIB) region (also called the p21 Binding Domain, PBD) of the Cdc42/Rac effector protein, p21 activated kinase 1 (PAK). The CRIB/PBD protein motif binds specifically to the GTP-bound form of Rac and/or Cdc42 proteins. The PBD region of PAK has a high affinity for both GTP-Rac and GTP-Cdc42 and that PAK binding results in a significantly reduced intrinsic and catalytic rate of hydrolysis of both Rac and Cdc42 making it an ideal tool for affinity purification of GTP-Rac and GTP-Cdc42 from cell lysates. The PAK-PBD protein in kit corresponds to residues 67-150. It includes the highly conserved CRIB region (aa 74-88) plus sequences required for the high affinity interaction with GTP-Rac and GTP-Cdc42. The PAK-PBD is in the form of a GST fusion protein, which allows "pull-down" of the PAK-PBD/GTP-Cdc42 (or GTP-Rac) complex with glutathione affinity beads. The assay provides a simple means of quantitating Rac/Cdc42 activation in cells. The amount of activated Cdc42 is determined by a Western blot using a Cdc42 specific antibody.

Results

Figure 6E:
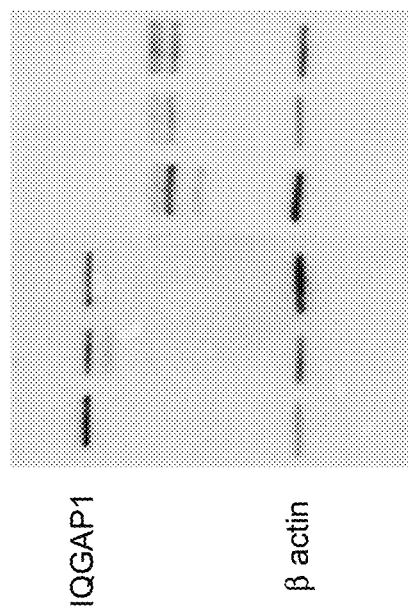
Figure 6D:
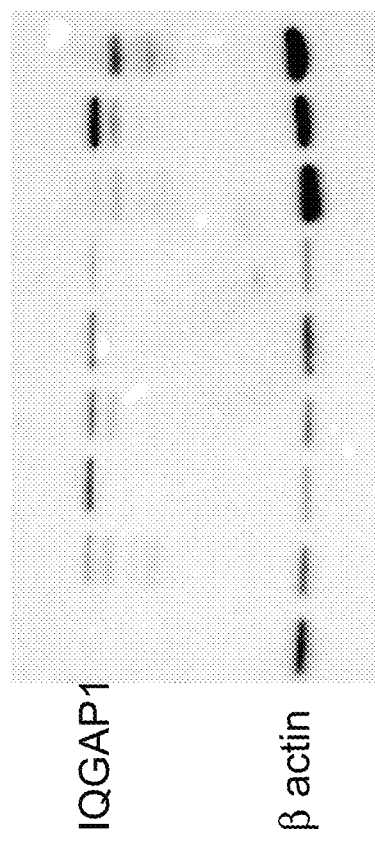

IQGAP1 is overexpressed in the majority of AML patients: Rabbits were immunized subcutaneously weekly× 16 weeks with FDNB modified as well as unmodified human WBC cells as shown in FIG. 6A. After heat inactivation of complement the immune sera were absorbed against pooled WBCs from normal healthy subjects. The absorbed immune sera were used to probe replicate Western blots of de-identified primary human AML samples. As shown in FIG. 6B serum from rabbits immunized with FDNB modified WBCs recognized a different set of antigens than the ones by serum from rabbit immunized with unmodified WBCs. Proteomic analysis of the affinity purified lysates of primary AML samples were done using the strategy of depletion followed by enrichment as shown in FIG. 6C. In experiments done with three separate AML samples and repeated on one of those three samples, IQGAP1 was noted to be differentially recognized. To confirm the findings, the expression levels of IQGAP1 in nine primary AML samples were investigated by Western blot analysis. As shown in the FIG. 6D, four of the nine samples showed high IQGAP1 expression, three samples showed moderate expression whereas the remaining two patient samples did not exhibit the expression of IQGAP1. Three normal bone samples did not express IQGAP1 (FIG. 6E)

IQGAP1 is overexpressed in leukemia cell-lines and AML patient samples compared to normal bone marrow: H&E staining and immunohistochemical staining for IQGAP1 was performed on three leukemia cell-lines (K562, MV411, THP1), bone marrow from two AML patients (AML #1 and AML #2) and two normal subjects. It showed increased expression of IQGAP1 in the cell lines and AML samples than normal bone marrow, which showed minimal to no expression of IQGAP1 (FIGS. 7A, 7B and 7C).

BloodSpot analysis showed that, as compared to normal hematopoietic cells, various subtypes of acute leukemia including acute promyelocytic leukemia (APL) [(AML t(15:17)], acute myeloid leukemia carrying inv(16)/t(16;16) chromosomal abnormalities, AML complex HSCs, acute myeloid leukemia with t(8;21) and 11q23 chromosomal abnormalities showed increased IQGAP1 expression (FIG. 7D).

Figure 8:
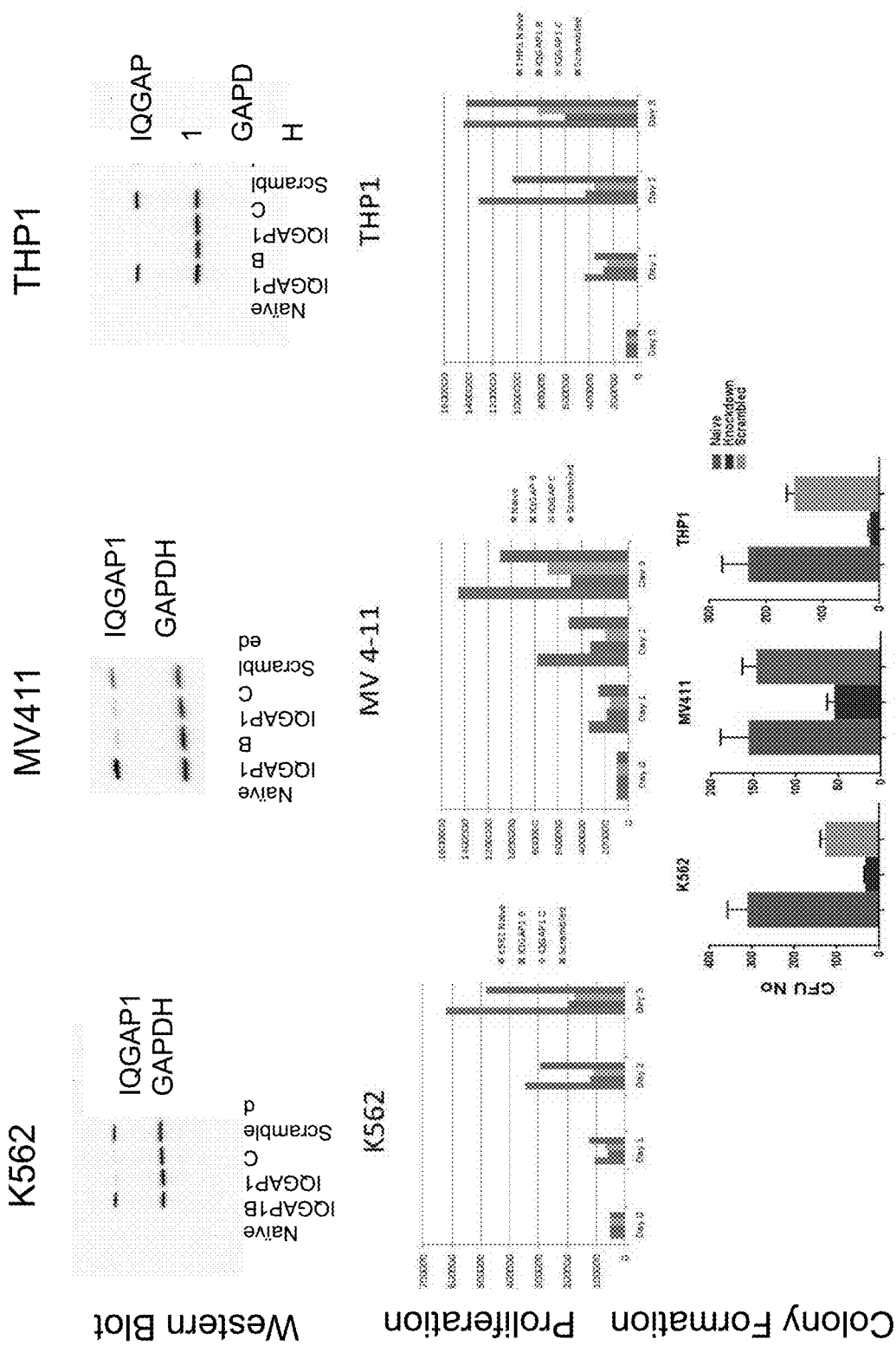
FIG. 8 depicts exemplary results demonstrating that IQGAP1 silencing via shRNA reduced colony proliferation and colony formation in three leukemia cell lines.

IQGAP1 silencing reduced proliferation and colony forming potential of leukemia cell-lines: Cells with IQGAP1 knockdown by shRNAs compared to cells transfected with scrambled shRNA and naïve cells (FIG. 8, top) blocked the proliferation of K652, MV411 and THP1 leukemia cells (FIG. 8, middle). Two sequentially different siRNAs against IQGAP1 were employed. Similarly, the shRNA mediated knockdown of IQGAP1 in K652, MV411 and THP1 leukemia cells showed reduced colony formation in the silenced group than the naïve cells or cells transfected with scrambled shRNA (FIG. 8, bottom).

Virtual screening identified potent small molecule inhibitor of IQGAP1: A virtual screening of 212,966 compounds was conducted as described in the Methods section. The exercise yielded four small molecules ranked between 5-54 based on their binding energy scores (FIG. 3). Hits identified as AK778 (rank 5), AB323 (rank 42) and AS871 (rank 54) were tested for their effects on the proliferation of leukemia cells (data not shown). Highest ranked hit (AK778) showed most potent inhibition of leukemia cells in the dose range tested (data not shown). To understand the structure-activity relationship of AK778 10 close structural analog of AK778 were obtained. Screening revealed UR778Br, the most potent structural analog of AK778. Installation of Bromine atom on the phenyl part of the indole ring enhanced the anti-proliferative activity of AK778 (FIG. 3).

UR778Br reduces proliferation of leukemia cell lines: Exposure of MOLM13, MV411, THP1 and U937 to a range of concentrations of UR778Br for 72 hours resulted in dose dependent reduction of proliferation as measured by counting cells in a hemocytometer as described in the Materials and Methods section (FIG. 9).

UR778Br reduces viability of leukemia cell lines: Exposure of MOLM13, MV411, THP1 and U937 to a range of concentrations of UR778Br for 48 hours resulted dose-dependent decrease in viability, measured by the MTS assay as described in the Materials and Methods section (FIG. 10).

UR778Br causes dose-dependent G2/M phase arrest and apoptosis in leukemia cell lines: MOLM13, MV411, THP1 and U937 cells were exposed to a range of concentrations of UR778Br for 24 hours. Cell cycle analyses performed as described showed dose-dependent arrest in G2/M phase of the cell cycle (FIGS. 11A-11D). There was apoptosis in the four cell lines upon exposure to UR778B2 25 µM for 24 hours as seen by expression of cleaved PARP, a marker of apoptosis (FIG. 11E).

UR778Br blocks colony formation of leukemia cell lines: Clonogenicity of leukemia cells (MOLM13, MV411, THP1, and U937) was measured in MethoCult Enriched, as described in materials and methods. The addition of UR778Br resulted in inhibition of the colony formation units of the cell lines at 6.25 µM concentration (FIGS. 12A-12D).

Figure 13:
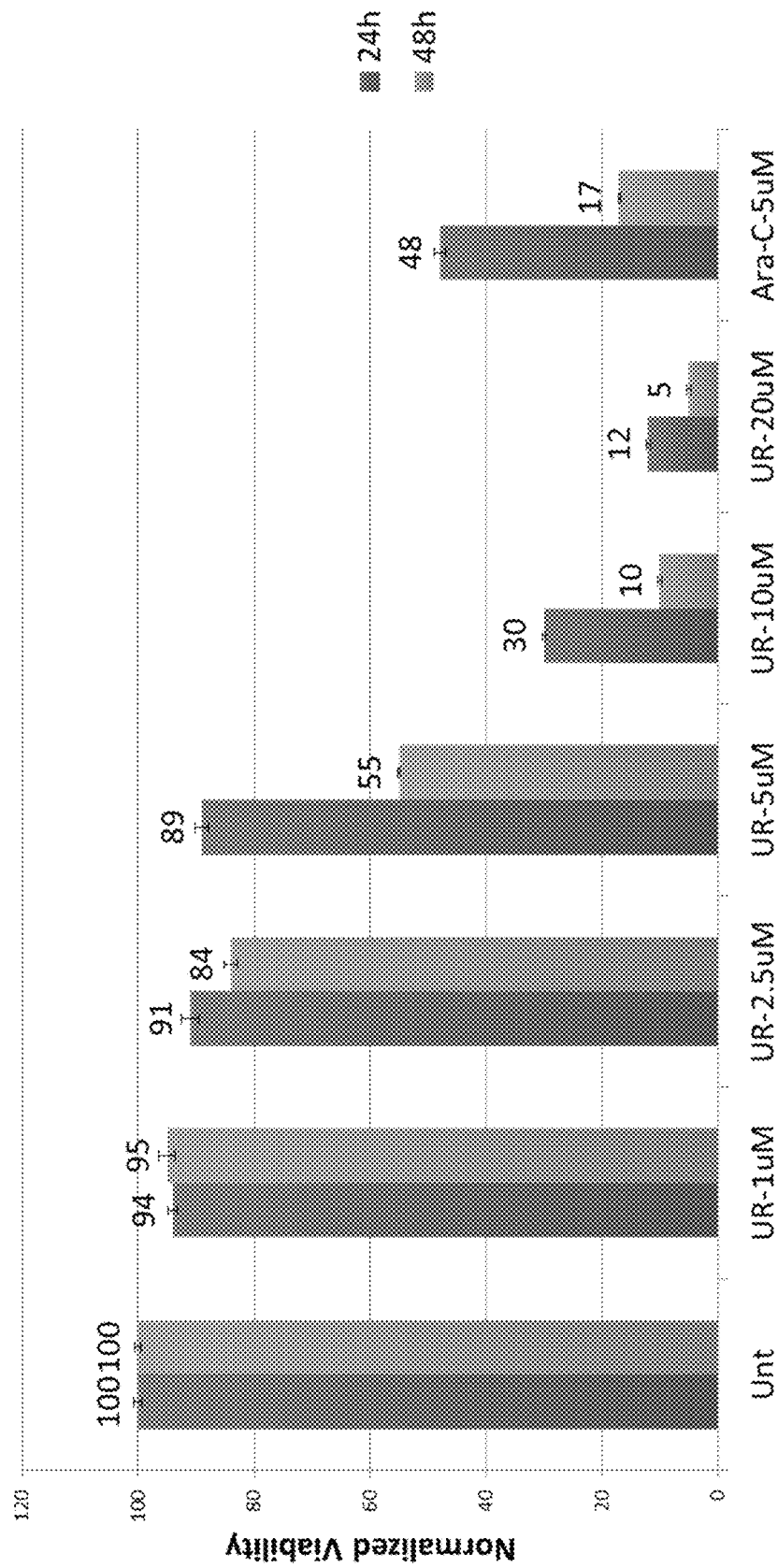
FIG. 13 depicts exemplary results demonstrating reduced viability of a primary AML sample treated for 24 or 48 hours with a range of concentrations of UR778Br and cytarabine 5 uM analyzed by flow cytometry.
Figure 13:
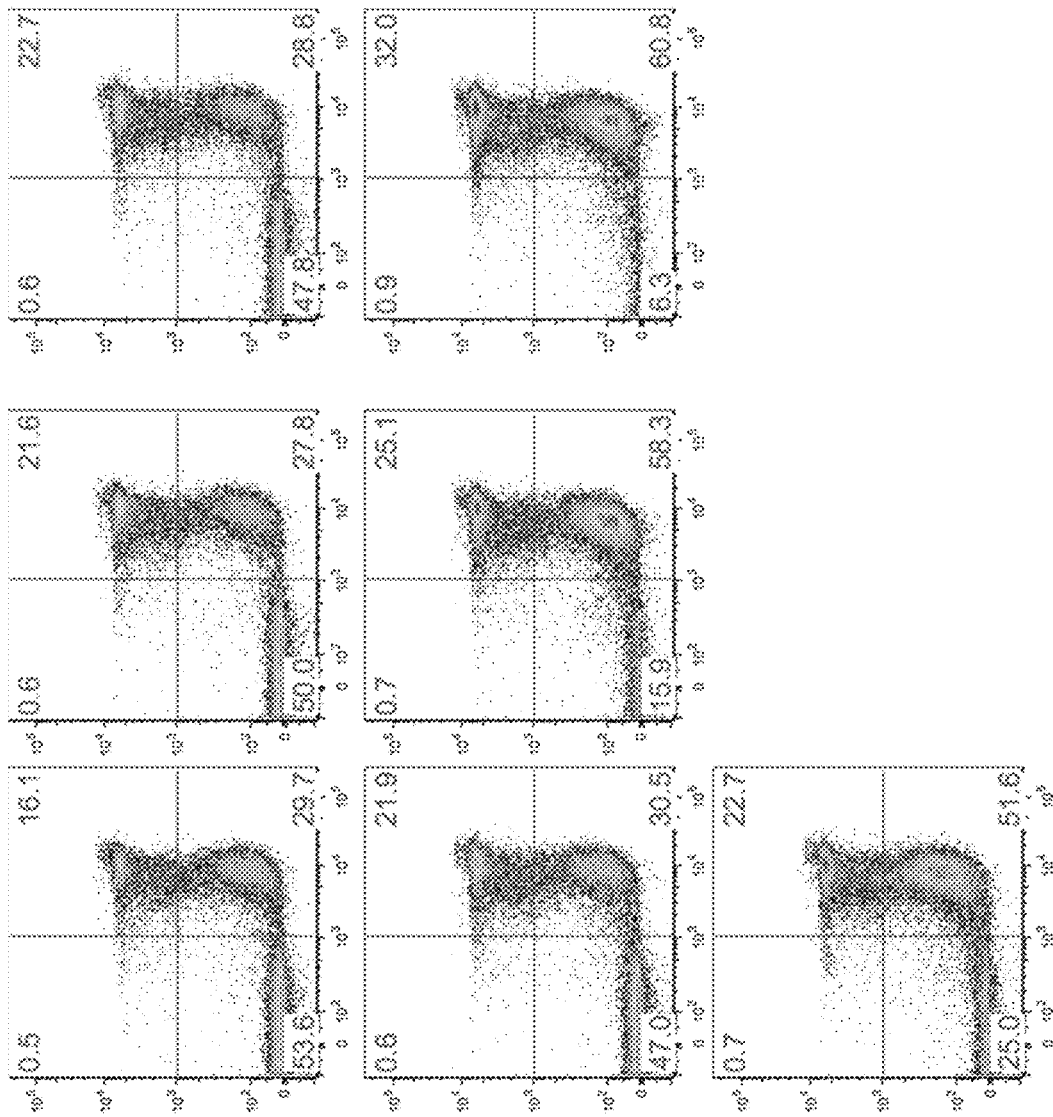
Figure 14:
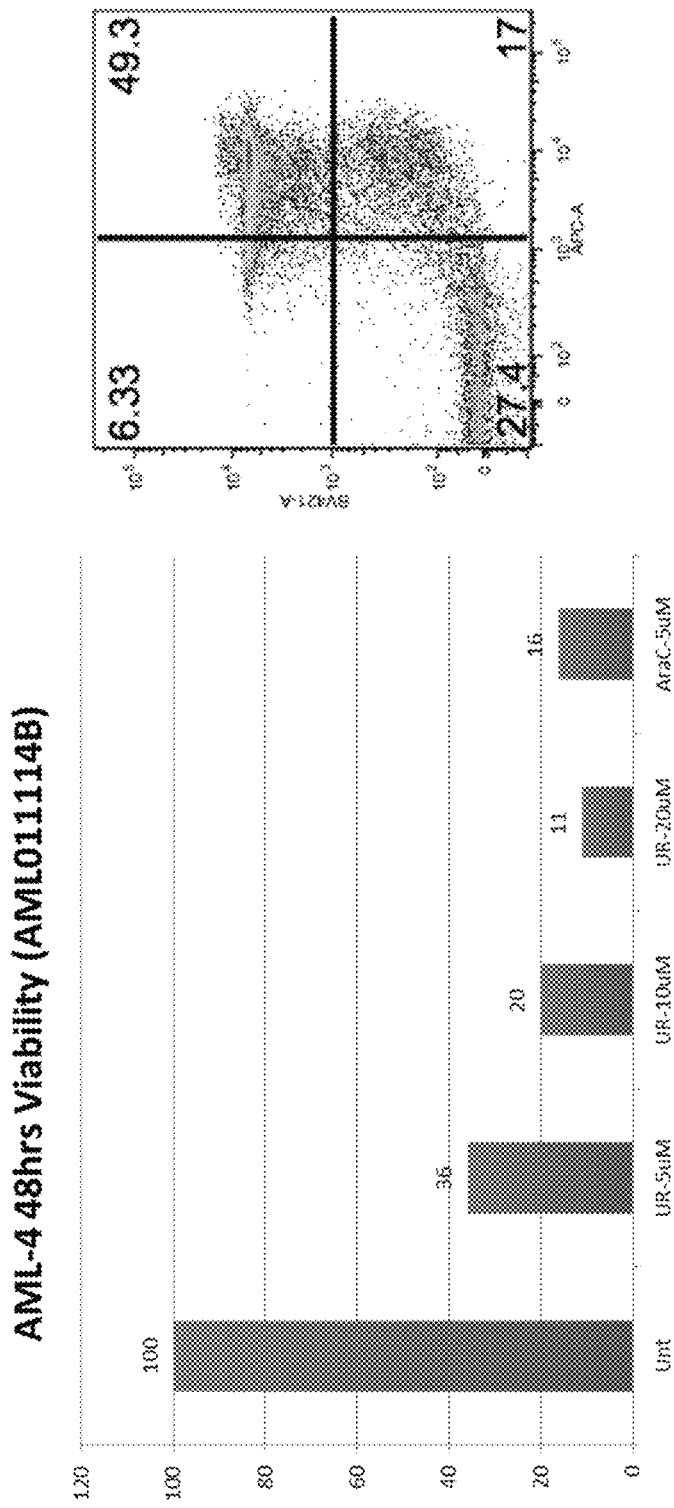
FIG. 14 depicts exemplary flow cytometry results demonstrating reduced viability of three additional sample of primary AML cells 48 hours after treatment.
Figure 14:
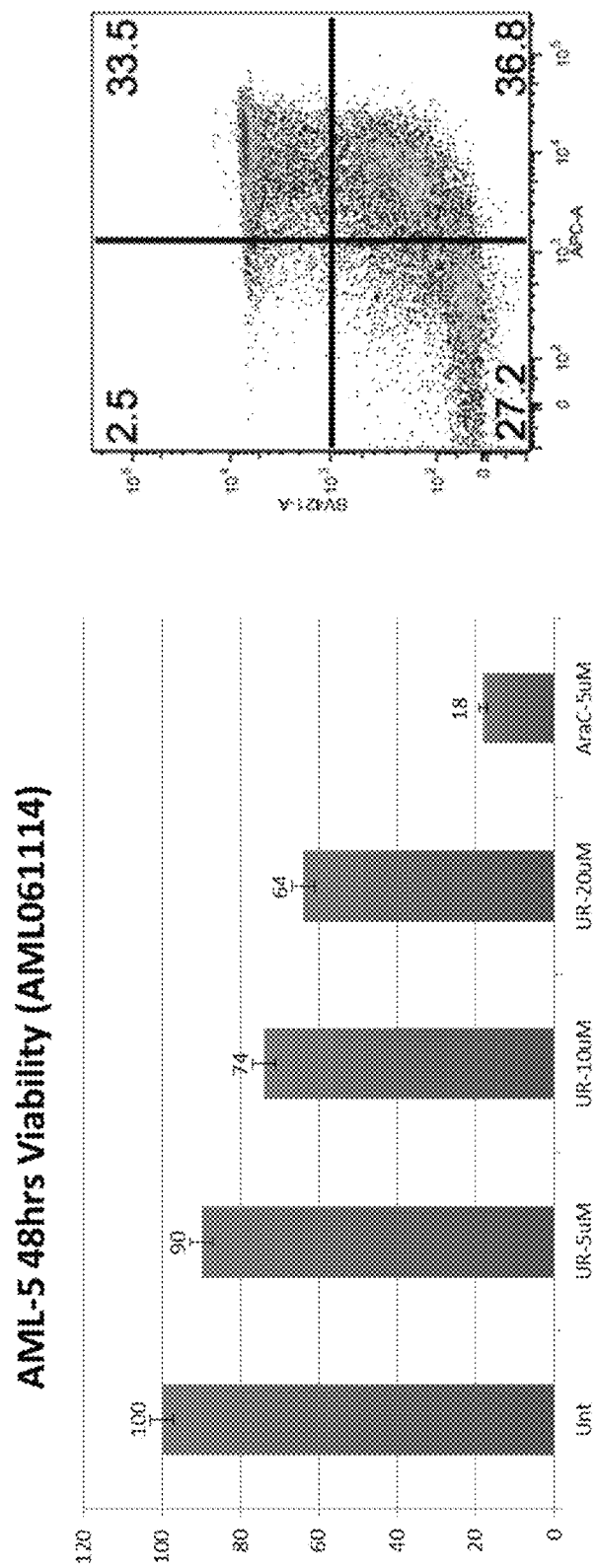

UR778Br causes dose-dependent decrease in viability in Primary AML cells: Primary AML cells were exposed to DMSO, UR778Br over a dose range and cytarabine (Ara-C) 5 µM for 24 hours and 48 hours. The cells were stained for annexin-V and DAPI and analyzed by flow cytometetry. Annexin-V and DAPI double negative cells were scored a viable (FIG. 13). In subsequent experiments viability was measured at 48 hours. There was dose dependent decrease in viability in three additional primary AML samples (FIG. 14).

Figure 15:
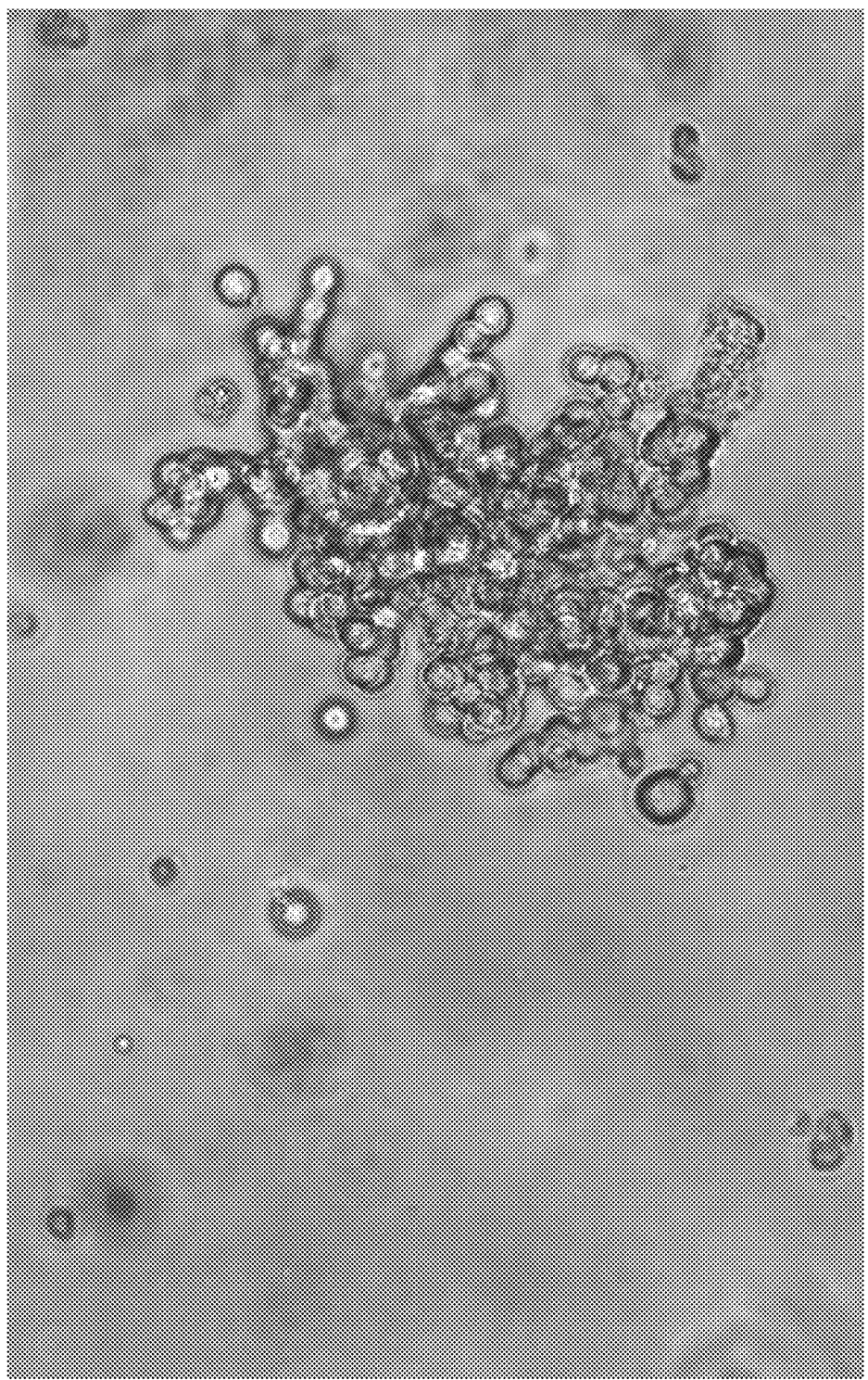
FIG. 15 depicts an exemplary micrograph demonstrating colony formation by a primary AML sample.
Figure 16:
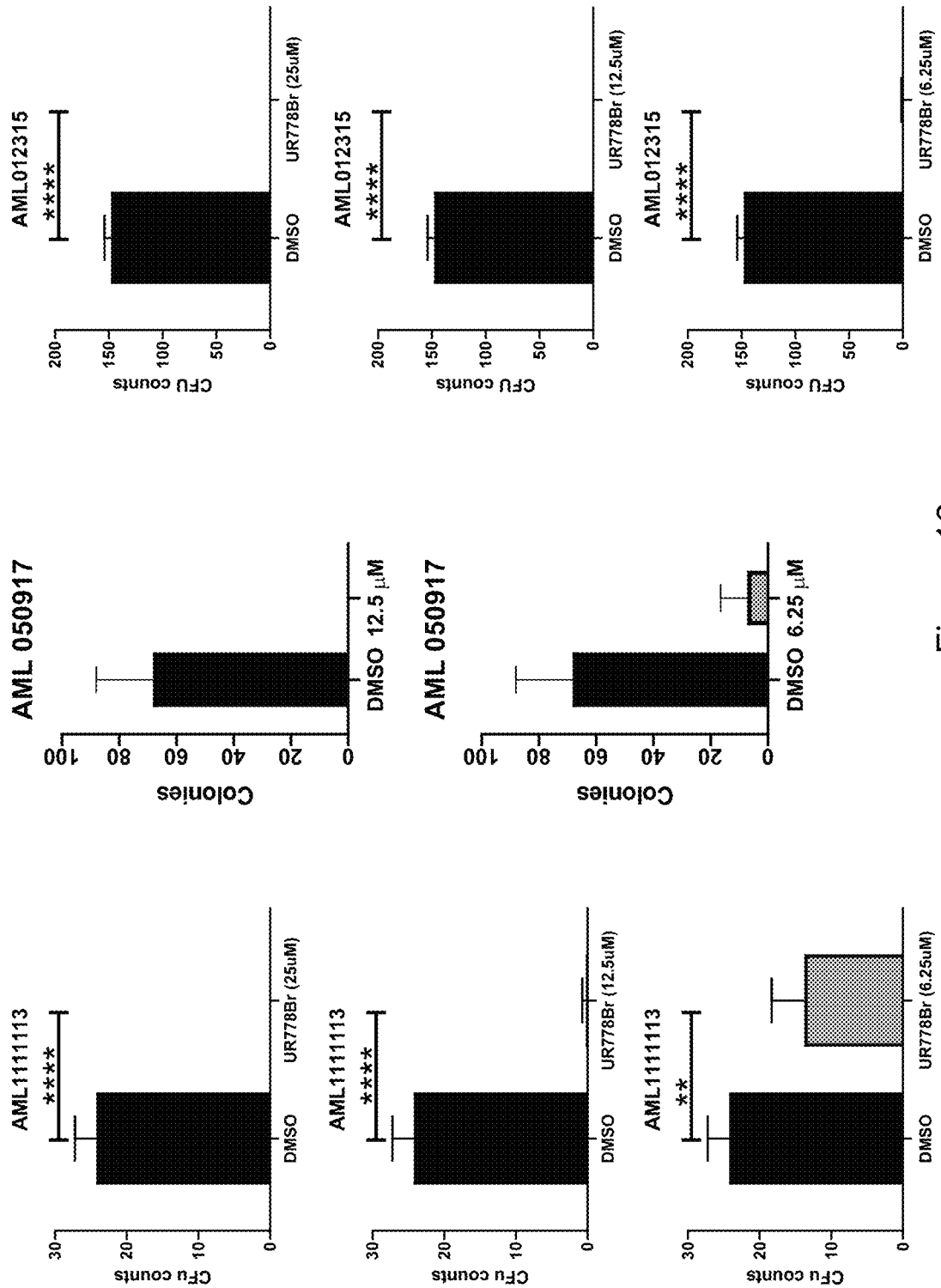
FIG. 16 depicts exemplary results demonstrating UR778Br blocks colony formation by three primary AML cells in the presence of concentrations as low as 6.25 µM.

UR778Br blocks colony formation by primary AML cells: Clonogenicity of primary AML cells exposed to DMSO, varying concentrations of UR778Br and cytarabine in MethoCult Enriched was measured as described in materials and methods. The addition of UR778Br resulted in inhibition of the colony formation units (FIG. 15 and FIG. 16).

UR778 did not decrease colony formation by normal primary bone marrow cells to the same degree: Clonogenicity of normal primary bone marrow cells exposed to DMSO, and varying concentrations of UR778Br in MethoCult Enriched was measured as described in materials and methods. The addition of UR778Br at 12.5 µM resulted in inhibition of the colony formation units to a greater degree than at 6.25 µM concentration (FIG. 22).

It is estimated that there will be 20,240 new cases and 11400 deaths from AML in 2021 (Siegel R L, et al., CA Cancer J Clin. 2021, 71(1):7-33). Analyses of SEER database reveal that over the 3 decades, from 1977 to 2006, overall relative survival has not improved in those aged ≥75 years (MSS Thein Cancer 2013). Identification of novel therapeutic target(s) and development of pharmacologic agents to the targets are needed to improve outcomes in AML in this age group.

Herein is reported that the scaffolding protein IQGAP1 is overexpressed in primary human AML cells compared to normal bone marrow (FIG. 6 and FIG. 12). Knocking down expression of IQGAP1 with shRNA decreased proliferation and colony formation by K562, MV411 and THP1 human leukemia cell lines (FIG. 8) indicating that IQGAP1 would be a therapeutic target in the human AML.

While the data show that IQGAP1 is a therapeutic target in AML, pharmacologic agents targeting signaling via IQGAP1 have not been previously described. Therefore, a virtual screening was conducted of over 212,000 small molecules predicted to target the GRD domain of IQGAP1 which binds to CDc41 and Rac1 and Rho A GTPases which are linked to leukemia genesis. UR778Br (FIG. 5), is a brominated analog of UR778, one of the four hits identified with highest score in the virtual screening. UR778Br decreased proliferation, viability, resulted in G2/M arrest and inhibited colony formation by human AML cell lines (FIGS. 9-13) as well as primary human AML cells in low micromolar range (FIGS. 14-16). Notably, it spared colony formation of normal bone marrow cells (FIG. 17).

In addition to AML, IQGAP1 is also overexpressed in colon cancer, pancreatic cancer, hepatocellular carcinoma, and glioma. Overexpression at protein level is associated with an aggressive clinical course in gastric cancer, lung cancer, glioma, and ovarian cancer. In addition to the data presented herein in AML, disabling the interaction of ERK1/2 with the WW domain of IQGAP1 was shown to effectively target RAS-MAP kinase-driven tumors (Khvari et al). A cell penetrating peptide targeting WW domain decreased the amount of ERK1/2 bound to IQGAP1 in vitro and impaired tumorigenesis in mice bearing MDA-MB-468 breast cancer and SK-Mel-28 melanoma tumors when administered systemically via an osmotic pump without causing any morbidity in mice.

While IQGAP1 is involved in multiple cellular processes it does not serve any essential non-redundant function as evidenced by the report by Li et al. that IQGAP1 null mutant mice arose at normal frequency and showed no defects during development and for most of their adult life except increase in late onset gastric hyperplasia relative to wild-type animals. Based on the results small molecule or other agents disrupting signaling via IQGAP1 would not be predicted to be very toxic.

In addition to selectivity to primary AML cells UR778Br has other critical drug-like characteristics such as log P(3.28), c Log P (4.84) and tPSA (total polar surface area: 77.84) along with a molecular weight of 417 that is less than 500 Dalton units. While not being bound by scientific theory, it is believed that studies to optimize the structure-activity relationships yield a novel structural class of orally bioavailable agents with high selectivity for AML while relatively sparing normal hematopoietic progenitor cells.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating acute myeloid leukemia in a subject having acute myeloid leukemia, wherein the method comprises administering to the subject a compound selected from the group consisting of:

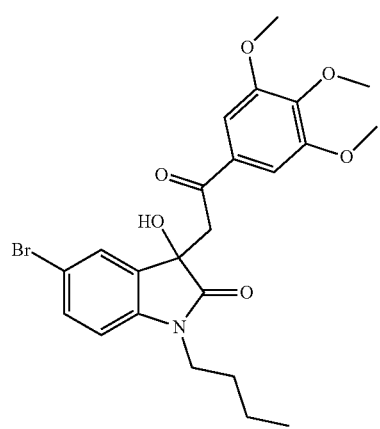

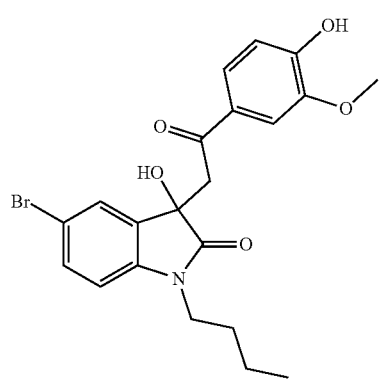

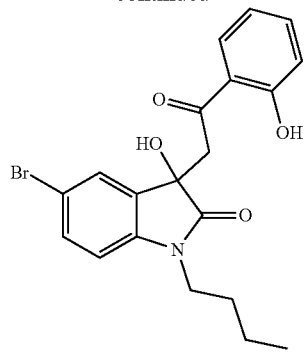

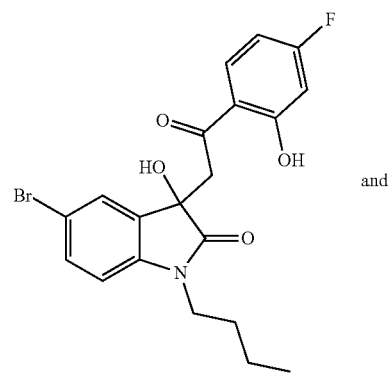

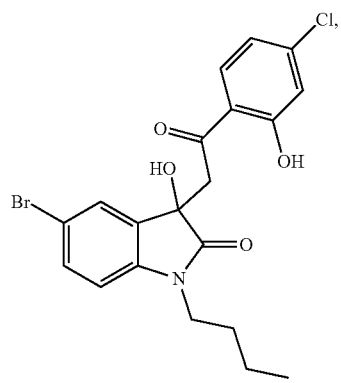

and or a pharmaceutically acceptable salt thereof.

2. The method of claim 1, wherein the compound is
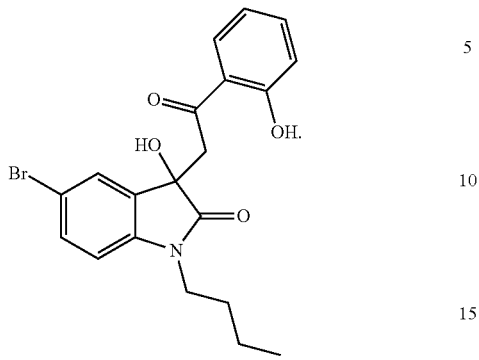
3. The method of claim 1, wherein the acute myeloid leukemia is associated with or caused by overexpression of IQGAP1.
* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Chemically synthesized

<400> SEQUENCE: 1
cctaaggtta agtcgccctc g                                             21

<210> SEQ ID NO 2
<211> LENGTH: 21
<212> TYPE: DNA

```
<213> ORGANISM: Artificial Sequence
<220> FEATURE:
<223> OTHER INFORMATION: Chemically synthesized

<400> SEQUENCE: 2
gcatccactt accaggatat a                              21

<210> SEQ ID NO 3
<211> LENGTH: 21
<212> TYPE: DNA
<213> ORGANISM: Artificial Sequence
<220> FEATURE:
<223> OTHER INFORMATION: Chemically synthesized

<400> SEQUENCE: 3
gcagctcctg agtgataaac a                              21
```